US010932938B2

(12) United States Patent
French

(10) Patent No.: US 10,932,938 B2
(45) Date of Patent: Mar. 2, 2021

(54) CLAMP INSTALLATION TOOL

(71) Applicant: Advanced Bariatric Technology, LLC, Coral Gables, FL (US)

(72) Inventor: C. Kenneth French, Dripping Springs, TX (US)

(73) Assignee: ADVANCED BARIATRIC TECHNOLOGY, LLC, Coral Gables, FL (US)

( * ) Notice: Subject to any disclaimer, the term of this patent is extended or adjusted under 35 U.S.C. 154(b) by 125 days.

(21) Appl. No.: 16/044,382

(22) Filed: Jul. 24, 2018

(65) Prior Publication Data

US 2019/0021892 A1    Jan. 24, 2019

Related U.S. Application Data

(60) Provisional application No. 62/536,364, filed on Jul. 24, 2017.

(51) Int. Cl.
    *A61F 5/00*          (2006.01)
    *A61B 17/128*      (2006.01)
    (Continued)

(52) U.S. Cl.
    CPC .......... *A61F 5/0089* (2013.01); *A61B 17/122* (2013.01); *A61B 17/1285* (2013.01);
    (Continued)

(58) Field of Classification Search
    CPC ................. A61F 5/0086; A61F 5/0089; A61B 2017/00818; A61B 2017/00477;
    (Continued)

(56) References Cited

U.S. PATENT DOCUMENTS

| 600,887 A | 3/1898 | Pettit |
|---|---|---|
| 3,254,651 A | 6/1966 | Collito |

(Continued)

FOREIGN PATENT DOCUMENTS

| AU | 201399422 | 2/2017 |
|---|---|---|
| AU | 2018247195 A1 | 11/2018 |

(Continued)

OTHER PUBLICATIONS

U.S. Appl. No. 15/642,919, Non-Final Office Action dated Aug. 6, 2019, 22 pgs.

(Continued)

*Primary Examiner* — Navin Natnithithadha
*Assistant Examiner* — Sunita Reddy
(74) *Attorney, Agent, or Firm* — Foley & Lardner LLP

(57) ABSTRACT

A clamp installation tool is provided. The tool may include a longitudinal main body, a selectable retention mechanism, and a tip manipulation member. The longitudinal main body may have an elongate member with a longitudinal support platform to support a clamp. The selectable retention mechanism may have a plurality of bosses to be received into corresponding apertures of the clamp, and the tip manipulation member may be coupled to a distal end of the longitudinal main body and arcuately articulable relative to the longitudinal main body. The tool may be operable to install a clamp inside a body cavity.

16 Claims, 28 Drawing Sheets

(51) Int. Cl.
   *A61B 17/122*  (2006.01)
   *A61B 17/00*  (2006.01)
   *A61B 17/29*  (2006.01)

(52) U.S. Cl.
   CPC .... *A61F 5/0086* (2013.01); *A61B 2017/0023* (2013.01); *A61B 2017/0042* (2013.01); *A61B 2017/00477* (2013.01); *A61B 2017/00818* (2013.01); *A61B 2017/2927* (2013.01)

(58) Field of Classification Search
   CPC ........ A61B 2017/2927; A61B 17/1285; A61B 17/122; A61B 2017/0023; A61B 2017/0042
   USPC .......................................................... 600/37
   See application file for complete search history.

(56) References Cited

U.S. PATENT DOCUMENTS

| | | | |
|---|---|---|---|
| 3,316,914 A | 5/1967 | Collito | |
| 3,417,752 A | 12/1968 | Butler | |
| 3,766,925 A | 10/1973 | Rubricius | |
| 4,060,089 A | 11/1977 | Noiles | |
| 4,274,415 A | 6/1981 | Kanamoto et al. | |
| 4,346,869 A | 8/1982 | MacNeill | |
| 4,390,019 A | 6/1983 | Leveen et al. | |
| 4,414,721 A | 11/1983 | Hufnagel | |
| 4,428,374 A | 1/1984 | Auburn | |
| 4,458,681 A | 7/1984 | Hopkins | |
| 4,548,202 A | 10/1985 | Duncan | |
| 4,558,699 A | 12/1985 | Bashour | |
| 4,610,250 A | 9/1986 | Green | |
| 4,803,985 A | 2/1989 | Hill | |
| 4,950,284 A | 8/1990 | Green et al. | |
| 4,976,721 A | 12/1990 | Blasnik et al. | |
| 5,062,846 A | 11/1991 | Oh et al. | |
| 5,074,868 A | 12/1991 | Kuzmak | |
| 5,127,915 A | 7/1992 | Mattson | |
| 5,156,609 A | 10/1992 | Nakao et al. | |
| 5,163,945 A | 11/1992 | Ortiz et al. | |
| 5,226,429 A | 7/1993 | Kuzmak | |
| 5,234,454 A | 8/1993 | Bangs | |
| 5,236,437 A | 8/1993 | Wilk et al. | |
| 5,250,058 A | 10/1993 | Miller et al. | |
| 5,327,914 A | 7/1994 | Shlain | |
| 5,345,949 A | 9/1994 | Shlain | |
| 5,423,831 A | 6/1995 | Nates | |
| 5,428,871 A | 7/1995 | Iosif | |
| 5,456,714 A | 10/1995 | Owen | |
| 5,464,416 A | 11/1995 | Steckel | |
| 5,549,621 A | 8/1996 | Bessler et al. | |
| 5,575,802 A | 11/1996 | McQuilkin et al. | |
| 5,766,189 A | 6/1998 | Matsuno | |
| 5,901,993 A | 5/1999 | Lowery et al. | |
| 6,036,704 A | 3/2000 | Yoon | |
| 6,102,922 A * | 8/2000 | Jakobsson | A61F 5/0003 606/157 |
| 6,179,850 B1 | 1/2001 | Goradia | |
| 6,273,903 B1 | 8/2001 | Wilk | |
| 6,454,700 B1 * | 9/2002 | Forsell | A61F 5/0003 600/37 |
| 6,464,710 B1 | 10/2002 | Foster | |
| 6,503,258 B1 | 1/2003 | Filho | |
| 6,537,289 B1 | 3/2003 | Kayan et al. | |
| 6,572,629 B2 | 6/2003 | Kalloo et al. | |
| 6,694,982 B2 | 2/2004 | Latour | |
| 6,716,226 B2 | 4/2004 | Sixto, Jr. et al. | |
| 6,814,742 B2 | 11/2004 | Kimura et al. | |
| 6,869,438 B2 | 3/2005 | Chao | |
| 6,926,724 B1 | 8/2005 | Chu | |
| 6,981,978 B2 | 1/2006 | Gannoe | |
| 7,022,126 B2 | 4/2006 | De Canniere | |
| 7,105,000 B2 | 9/2006 | McBrayer | |
| 7,135,032 B2 | 11/2006 | Åkerfeldt | |
| 7,214,233 B2 | 5/2007 | Gannoe et al. | |
| 7,223,229 B2 | 5/2007 | Inman et al. | |
| 7,232,445 B2 | 6/2007 | Kortenbach et al. | |
| 7,261,725 B2 | 8/2007 | Binmoeller | |
| 7,288,100 B2 | 10/2007 | Molina Trigueros | |
| 7,320,701 B2 | 1/2008 | Haut et al. | |
| 7,338,503 B2 | 3/2008 | Rosenberg et al. | |
| 7,416,528 B2 | 8/2008 | Crawford et al. | |
| 7,645,285 B2 | 1/2010 | Cosgrove et al. | |
| 7,691,053 B2 | 4/2010 | Viola | |
| 7,758,493 B2 | 7/2010 | Gingras | |
| 7,871,416 B2 | 1/2011 | Phillips | |
| 7,892,244 B2 | 2/2011 | Monassevitch et al. | |
| 8,287,559 B2 | 10/2012 | Barker et al. | |
| 8,382,775 B1 | 2/2013 | Bender et al. | |
| 8,529,585 B2 | 9/2013 | Jacobs et al. | |
| 8,920,305 B2 | 12/2014 | Jacobs et al. | |
| 9,808,257 B2 | 11/2017 | Armenteros et al. | |
| 9,814,614 B2 | 11/2017 | Jacobs et al. | |
| 10,369,036 B2 | 8/2019 | Jacobs et al. | |
| 10,420,664 B2 | 9/2019 | Armenteros et al. | |
| 10,456,141 B2 | 10/2019 | Armenteros et al. | |
| 2002/0022851 A1 | 2/2002 | Kalloo et al. | |
| 2002/0055757 A1 * | 5/2002 | Torre | A61B 17/12136 606/192 |
| 2002/0082625 A1 | 6/2002 | Huxel et al. | |
| 2002/0138086 A1 | 9/2002 | Sixto et al. | |
| 2004/0010271 A1 * | 1/2004 | Kortenbach | A61B 1/00179 606/139 |
| 2004/0059289 A1 * | 3/2004 | Garza Alvarez | A61B 17/12099 604/96.01 |
| 2004/0082963 A1 | 4/2004 | Gannoe et al. | |
| 2004/0097989 A1 | 5/2004 | Molina Trigueros | |
| 2004/0116945 A1 | 6/2004 | Sharkawy et al. | |
| 2004/0147942 A1 | 7/2004 | Chao | |
| 2005/0075652 A1 | 4/2005 | Byrum et al. | |
| 2005/0119674 A1 | 6/2005 | Gingras | |
| 2005/0125014 A1 | 6/2005 | Duluco et al. | |
| 2005/0149069 A1 | 7/2005 | Bertolero et al. | |
| 2005/0192599 A1 | 9/2005 | Demarais | |
| 2005/0197714 A1 | 9/2005 | Sayet | |
| 2005/0216042 A1 | 9/2005 | Gertner | |
| 2005/0250980 A1 | 11/2005 | Swanstrom et al. | |
| 2005/0251158 A1 | 11/2005 | Saadat et al. | |
| 2005/0277959 A1 | 12/2005 | Cosgrove et al. | |
| 2006/0011699 A1 | 1/2006 | Olson et al. | |
| 2006/0074440 A1 | 4/2006 | Garner | |
| 2006/0157067 A1 | 7/2006 | Saadat et al. | |
| 2006/0178564 A1 * | 8/2006 | Jones | A61F 5/0003 600/159 |
| 2006/0200179 A1 | 9/2006 | Barker et al. | |
| 2006/0217757 A1 | 9/2006 | Horndeski | |
| 2006/0241653 A1 * | 10/2006 | Jones | A61F 5/005 606/125 |
| 2006/0252983 A1 | 11/2006 | Lembo et al. | |
| 2006/0264981 A1 | 11/2006 | Viola | |
| 2006/0264982 A1 | 11/2006 | Viola et al. | |
| 2006/0264987 A1 | 11/2006 | Sgro | |
| 2007/0016231 A1 | 1/2007 | Jambor et al. | |
| 2007/0021761 A1 | 1/2007 | Phillips | |
| 2007/0032807 A1 | 2/2007 | Ortiz et al. | |
| 2007/0088190 A1 | 4/2007 | Appel | |
| 2007/0088191 A1 * | 4/2007 | Appel | A61F 5/0003 600/37 |
| 2007/0149989 A1 | 6/2007 | Santilli et al. | |
| 2007/0167962 A1 | 7/2007 | Gannoe et al. | |
| 2007/0185373 A1 | 8/2007 | Tsonton | |
| 2007/0213747 A1 | 9/2007 | Monassevitch et al. | |
| 2007/0233005 A1 * | 10/2007 | McMichael | A61J 15/0015 604/164.01 |
| 2007/0250090 A1 * | 10/2007 | Makower | A61B 17/072 606/157 |
| 2007/0265644 A1 | 11/2007 | Ichihara et al. | |
| 2007/0282356 A1 * | 12/2007 | Sonnenschein | A61B 17/068 606/153 |
| 2008/0033457 A1 | 2/2008 | Francischelli et al. | |
| 2008/0039879 A1 | 2/2008 | Chin et al. | |

(56) References Cited

U.S. PATENT DOCUMENTS

| | | | |
|---|---|---|---|
| 2008/0082114 A1 | 4/2008 | McKenna et al. | |
| 2008/0092910 A1 | 4/2008 | Brooks | |
| 2008/0177292 A1 | 7/2008 | Jacobs et al. | |
| 2008/0208324 A1 | 8/2008 | Glithero et al. | |
| 2008/0269788 A1 | 10/2008 | Phillips | |
| 2008/0275480 A1* | 11/2008 | Jacobs | A61B 17/122 606/157 |
| 2008/0287975 A1* | 11/2008 | Weaner | A61F 5/0056 606/157 |
| 2008/0287976 A1 | 11/2008 | Weaner et al. | |
| 2008/0319435 A1 | 12/2008 | Rioux et al. | |
| 2009/0012542 A1* | 1/2009 | N'diaye | A61F 5/0079 606/153 |
| 2009/0137870 A1 | 5/2009 | Bakos et al. | |
| 2009/0138009 A1 | 5/2009 | Viswanathan et al. | |
| 2009/0198266 A1 | 8/2009 | Cesare | |
| 2009/0240105 A1* | 9/2009 | Smit | A61F 5/0089 600/104 |
| 2009/0281377 A1* | 11/2009 | Newell | A61B 17/07292 600/104 |
| 2009/0292163 A1 | 11/2009 | Kassab et al. | |
| 2010/0030017 A1 | 2/2010 | Baker et al. | |
| 2010/0082050 A1 | 4/2010 | Kassab et al. | |
| 2010/0168768 A1* | 7/2010 | Sonnenschein | A61B 17/072 606/139 |
| 2010/0174295 A1 | 7/2010 | Kassab et al. | |
| 2010/0312050 A1* | 12/2010 | Forsell | A61F 5/0073 600/37 |
| 2011/0046641 A1 | 2/2011 | Kassab et al. | |
| 2011/0092993 A1 | 4/2011 | Jacobs | |
| 2011/0092998 A1 | 4/2011 | Hirszowicz et al. | |
| 2011/0098732 A1 | 4/2011 | Jacobs | |
| 2011/0112434 A1* | 5/2011 | Ghabrial | A61B 17/3423 600/564 |
| 2011/0172767 A1* | 7/2011 | Rathi | A61B 17/0401 623/11.11 |
| 2011/0190791 A1* | 8/2011 | Jacobs | A61B 17/122 606/139 |
| 2011/0245593 A1 | 10/2011 | Kassab et al. | |
| 2011/0270016 A1* | 11/2011 | Snow | A61F 5/005 600/37 |
| 2012/0095484 A1 | 4/2012 | Dominguez | |
| 2012/0123463 A1 | 5/2012 | Jacobs | |
| 2012/0215061 A1 | 8/2012 | Fridez et al. | |
| 2013/0261382 A1 | 10/2013 | Acosta | |
| 2014/0012293 A1 | 1/2014 | Bertolero et al. | |
| 2014/0046345 A1* | 2/2014 | Armenteros | A61B 17/0643 606/139 |
| 2014/0074131 A1* | 3/2014 | Armenteros | A61B 17/122 606/157 |
| 2014/0200598 A1 | 7/2014 | Kassab et al. | |
| 2014/0350664 A1* | 11/2014 | Tozzi | A61F 2/2442 623/2.11 |
| 2015/0038794 A1* | 2/2015 | Pattison | A61B 17/3462 600/204 |
| 2015/0051624 A1* | 2/2015 | Jacobs | A61B 17/122 606/157 |
| 2015/0150595 A1* | 6/2015 | Pattison | A61B 17/0218 600/204 |
| 2016/0058594 A1* | 3/2016 | Armenteros | A61B 17/1285 600/37 |
| 2017/0258619 A1 | 9/2017 | Jacobs et al. | |
| 2017/0360447 A1 | 12/2017 | Armenteros et al. | |
| 2018/0008447 A1 | 1/2018 | Jacobs et al. | |
| 2019/0358067 A1 | 11/2019 | Jacobs et al. | |
| 2019/0358068 A1 | 11/2019 | Armenteros et al. | |
| 2020/0054340 A1 | 2/2020 | Armenteros et al. | |

FOREIGN PATENT DOCUMENTS

| | | |
|---|---|---|
| AU | 2017200911 | 12/2018 |
| AU | 2015306617 | 2/2020 |
| CA | 2880155 | 2/2014 |
| CN | 105007838 | 10/2015 |
| CN | 107072660 | 8/2017 |
| CN | 109316221 A | 2/2019 |
| CO | 30415 | 12/2016 |
| DE | 19751733 | 12/1998 |
| DE | 29822558 | 2/1999 |
| EP | 0 201 344 | 11/1986 |
| EP | 0 220 643 | 5/1987 |
| EP | 1 397 998 | 3/2004 |
| EP | 1 547 529 | 6/2005 |
| EP | 1 600 108 | 11/2005 |
| EP | 1 749 506 | 2/2007 |
| EP | 1 806 101 | 7/2007 |
| EP | 1 882 451 | 1/2008 |
| EP | 2 528 512 B1 | 12/2012 |
| EP | 3 185 784 | 7/2017 |
| EP | 3 398 538 | 11/2018 |
| EP | 2 882 354 B2 | 9/2020 |
| JP | 9289989 | 11/1997 |
| JP | 2002085414 | 3/2002 |
| JP | 2007044517 | 2/2007 |
| JP | 2007097664 | 4/2007 |
| JP | 2007159794 | 6/2007 |
| MX | 371177 | 1/2020 |
| NZ | 704680 | 5/2017 |
| RU | 2262896 C2 | 6/2005 |
| RU | 2386455 | 4/2010 |
| RU | 2626875 | 8/2017 |
| RU | 2703508 A | 10/2019 |
| RU | 2019131501 A | 11/2019 |
| SA | 6733 B | 12/2019 |
| TH | 158414 | 12/2016 |
| TH | 174586 | 3/2018 |
| WO | WO-80/01752 A1 | 9/1980 |
| WO | WO-1998/033437 | 8/1998 |
| WO | WO-9833437 | 8/1998 |
| WO | WO-1999/11179 | 3/1999 |
| WO | WO-9911179 | 3/1999 |
| WO | WO-2000/078234 | 12/2000 |
| WO | WO-0078234 | 12/2000 |
| WO | WO-2000076432 | 12/2000 |
| WO | WO-2002/064041 | 8/2002 |
| WO | WO-2004017839 | 3/2004 |
| WO | WO-2005/046453 A2 | 5/2005 |
| WO | WO-2006/033385 | 3/2006 |
| WO | WO-2006/044640 | 4/2006 |
| WO | WO-2007013995 | 2/2007 |
| WO | WO-2008081436 | 7/2008 |
| WO | WO-2008091537 | 7/2008 |
| WO | WO-2008101048 | 8/2008 |
| WO | WO-2011/094700 | 8/2011 |
| WO | WO-2014/026170 | 2/2014 |
| WO | WO-2016/033221 | 3/2016 |
| WO | WO-2018/009669 | 1/2018 |
| WO | WO-2019/023279 A1 | 1/2019 |

OTHER PUBLICATIONS

International Pat. Appl. No. PCT/US2018/043562, International Preliminary Report on Patentability dated Jan. 28, 2020, 9 pgs.

U.S. Appl. No. 15/642,919, Final Office Action dated Jan. 29, 2020, 22 pgs.

U.S. Appl. No. 15/677,227, Non-Final Office Action dated Nov. 27, 2019, 9 pgs.

U.S. Appl. No. 14/836,621, Advisory Action dated Apr. 10, 2019, 6 pgs.

U.S. Appl. No. 14/836,621, Notice of Allowance, dated Apr. 30, 2019, 13 pgs.

U.S. Appl. No. 13/963,998, Final Office Action dated Feb. 7, 2019, 36 pgs.

U.S. Appl. No. 14/836,621, Final Office Action dated Jan. 31, 2019, 11 pgs.

"A Pathway to Endoscopic Bariatric Therapies" Gastrointestinal Endoscopy Journal, www.giejournal.org, vol. 74, No. 5 (2011), pp. 943-953.

An espace English abstract of DE-19751733 (Dec. 10, 1998).

An espace English abstract of JP-2007097664-A (Apr. 19, 2007).

(56) References Cited

OTHER PUBLICATIONS

An espace English abstract of JP-2007159794-A (Jun. 28, 2007).
An espace English abstract of JP-9289989-A (Nov. 11, 1997).
Certificate of Grant of copending Singapore Application No. SG11201500782R, dated Jun. 15, 2017.
Copending International Patent Application No. PCT/US2013/54435 filed Aug. 9, 2013, entitled "Polymer Overmolded Bariatric Clamp and Method of Installing"; First Named Inventor: Armenteros, Jesus R.
Copending International Patent Application No. PCT/US2015/47005 filed Aug. 26, 2015; First Named Inventor: Moises Jacobs.
Copending International Patent Application No. PCT/US17/40908 filed Jul. 6, 2017; First Named Inventor: Jesus R. Armenteros.
Copending U.S. Appl. No. 13/963,998, filed Aug. 9, 2013; Inventors: Jesus R. Armenteros et al.
Copending U.S. Appl. No. 14/021,720, filed Sep. 9, 2013; Inventors: Jesus R. Armenteros et al.
Copending U.S. Appl. No. 14/531,300, filed Nov. 3, 2014; Inventors: Moises Jacobs et al.
Copending U.S. Appl. No. 14/836,621, filed Aug. 26, 2015; First-Named Inventor: Jesus R. Armenteros.
Copending U.S. Appl. No. 15/605,812, filed May 25, 2017; First-Named Inventor: Moises Jacobs.
Copending U.S. Appl. No. 15/642,919, filed Jul. 6, 2017; First-Named Inventor: Moises Jacobs.
Copending U.S. Appl. No. 15/677,227, filed Aug. 15, 2017; First-Named Inventor: Jes\'fas R. Armenteros.
Copending U.S. Appl. No. 62/042,117, filed Aug. 26, 2014; first named inventor: Jesus R. Armenteros.
Copending U.S. Appl. No. 62/118,455, filed Feb. 19, 2015; first named inventor: Jesus R. Armenteros.
Copending U.S. Appl. No. 62/536,364, filed Jul. 24, 2017; first named inventor: C. Kenneth French.
Copending U.S. Appl. No. 62/359,529, filed Jul. 7, 2016; first named inventor: Jesus R. Armenteros.
Final Office Action cited in U.S. Appl. No. 11/984,452 dated Jan. 30, 2014.
Final Office Action cited in U.S. Appl. No. 11/984,452, dated Jan. 31, 2013 (12 pgs).
Final Office Action cited in U.S. Appl. No. 11/964,452, dated Mar. 26, 2010 (11 pgs).
Final Office Action for U.S. Appl. No. 13/963,998 dated Apr. 18, 2017 (16 pgs).
Final Office Action for U.S. Appl. No. 14/021,720 dated Jul. 14, 2016 (14 pgs).
freedictionary.com definition of "stretchable", accessed on Aug. 2, 2017, http://www.thefreedictionary.com/stretchable.
Geoffrey W.J. Vertical Ligated Gastroplasty by Clamp, Cut and Suture: A Series of 504 Cases Dating Back to 1977.0bes Surg. Nov. 1994;4(4):344-348, PMID: 10742799 [PubMed-as supplied by publisher], 5 pgs.
Helmut Kapczynski, Surgical Instruments 101, An Introduction to Kmedic Certified Instruments, Kmedic, Inc., 1997, Northvale, New Jersey (181 Pages).
International Preliminary Report on Patentability cited in PCT/US2008/000644, dated Nov. 17, 2009 (4 pgs).
International Preliminary Report on Patentability cited in PCT/US2011/023205, dated Jul. 31, 2012 (10 pgs).
International Preliminary Report on Patentability cited in PCT/US2013/054435, dated Jun. 9, 2015 (9 pgs).
International Preliminary Report on Patentability of PCT/US2015/047005, dated Mar. 9, 2017.
International Search Report and Written Opinion of PCT/US17/40908, dated Sep. 11, 2017.
International Search Report and Written Opinion of PCT/US18/43562, dated Nov. 21, 2018, 17 pgs.
International Search Report and Written Opinion of PCT/US2015/047005, dated Nov. 27, 2015.
International Search Report cited in PCT/US2013/54435, dated Jan. 16, 2014 (2 pgs).
International Search Report dated Nov. 27, 2015 in corresponding PCT Appln. PCT/US2015/047005, 13 pages.
Jacobs, Moises, et al., Presentation, "A Novel Procedure for Bariatric and Metabolic Surgery, a weight loss clamp" Apr. 2015 (20 pgs).
Machine Translation of DE29822558 U1.
Notice of Acceptance in AU Application No. 2013299422, (dated Nov. 1, 2016), 2 pgs.
Notice of Allowance for U.S. Appl. No. 14/021,720 dated May 16, 2016 (5 pgs).
Notice of Allowance for U.S. Appl. No. 14/021,720 dated Dec. 27, 2016 (8 pgs).
Notice of Allowance for U.S. Appl. No. 14/531,300 dated Apr. 12, 2016 (7 pgs).
Notice of Allowance for U.S. Appl. No. 14/531,300 dated Oct. 24, 2016 (7 pgs).
Notice of Allowance in U.S. Appl. No. 11/984,452 dated Jun. 30, 2014.
Office Action cited in U.S. Appl. No. 11/984,452, dated May 20, 2013 (14 pgs).
Office Action cited in U.S. Appl. No. 11/984,452, dated Aug. 6, 2012 (10 pgs).
Office Action cited in U.S. Appl. No. 11/984,452, dated Aug. 5, 2009 (13 pgs).
Office Action for U.S. Appl. No. 13/963,998 dated Nov. 15, 2016 (13 pgs).
Office Action for U.S. Appl. No. 14/021,720 dated Jan. 2, 2015 (8 pgs).
Office Action for U.S. Appl. No. 14/021,720 dated Jun. 12, 2015 (9 pgs).
Office Action for U.S. Appl. No. 14/021,720 dated Oct. 7, 2014 (6 pgs).
Office Action for U.S. Appl. No. 11/797,537 dated Jul. 16, 2009 (10 pages).
Office Action for U.S. Appl. No. 11/797,537 dated Jan. 7, 2010 (9 pages).
Office Action for U.S. Appl. No. 14/531,300 dated Oct. 19, 2015 (7 pages).
Office Action for U.S. Appl. No. 14/531,300 dated Dec. 29, 2014 (14 pages).
Office Action Restriction Requirement for U.S. Appl. No. 13/963,998 dated Jun. 1, 2016 (8 pgs).
Office Action, Translation and Search Report in Russian Patent Application No. 2015108054, (dated May 27, 2016), 6 pgs.
Patent Abstract of Japan of JP-2002085414-A (Mar. 26, 2002).
Patent Abstract of Japan of JP-2007044517-A (Feb. 22, 2007).
PCT International Search Report and Written Opinion cited in Patent Application No. PCT/US2011/023205, dated Apr. 5, 2011 (13 pgs).
PCT International Search Report cited in Patent Application No. PCT/US2008/000644, dated Jul. 7, 2008 (1 pg).
Publication of Co-Pending Singapore Patent Application No. 10201704073T, Jun. 29, 2017, 1 pg.
Rule 312 Amendment for U.S. Appl. No. 14/531,300 dated Jun. 8, 2016 (3 pgs).
Search Report of copending Singapore Application No. SG11201500782R, dated Oct. 8, 2015.
Shalimov, et al., Intestinal Track Surgery, Kiev, "Dzorovya", 1987, c. 558, 2 pgs.
U.S. Appl. No. 13/963,998, Final Office Action dated Apr. 18, 2018 (29 pgs).
U.S. Appl. No. 13/963,998, Non-Final Office Action dated Aug. 8, 2018 (36 pgs).
U.S. Appl. No. 13/963,998, Non-Final Office Action dated Aug. 21, 2017 (23 pgs).
U.S. Appl. No. 15/605,812, Final Office Action dated Jan. 19, 2018 (18 pages).
U.S. Appl. No. 15/605,812, Non-Final Office Action dated May 18, 2018 (27 pages).
U.S. Appl. No. 15/605,812, Non-Final Office Action dated Aug. 7, 2017 (14 pages).
U.S. Appl. No. 14/836,621, Final Office Action dated Mar. 16, 2018 (17 pgs.).

(56) References Cited

OTHER PUBLICATIONS

U.S. Appl. No. 14/836,621, Non-Final Office Action dated Jul. 6, 2018 (13 pgs).
U.S. Appl. No. 14/836,621, Non-Final Office Action dated Aug. 22, 2017 (16 pgs).
Written Opinion cited in PCT/US2008/000644, dated Jul. 7, 2008 (3 pgs).
Written Opinion cited in PCT/US2013/54435 dated Jan. 16, 2014 (8 pgs).
Written Opinion of copending Singapore Application No. SG11201500782R, dated Oct. 12, 2015.
U.S. Appl. No. 15/642,919, filed Jul. 6, 2017, Inflatable Bariatric Clamp.
U.S. Appl. No. 15/677,227, filed Aug. 15, 2017, Surgical Clamp and Surgical Clamp Installation Tool.
U.S. Appl. No. 16/533,309, filed Aug. 6, 2019, Bariatric Clamp With Suture Portions, Magnetic Inserts and Curvature.
U.S. Appl. No. 16/531,974, filed Aug. 5, 2019, Vertically Oriented Band for Stomach.
U.S. Appl. No. 16/664,447, filed Oct. 25, 2019, Polymer Overmolded Bariatric Clamp and Method of Installing.
U.S. Appl. No. 15/642,919, Non-Final Office Action dated Apr. 30, 2020, 30 pgs.
PCT International Patent Application No. PCT/US2017/040908, International Preliminary Report on Patentability and Notification dated Jan. 17, 2019, 9 pgs.
U.S. Appl. No. 15/605,812, Final Office Action dated Dec. 27, 2018, 22 pgs.
U.S. Appl. No. 13/963,998, Notice of Allowance, dated May 30, 2019, 11 pgs.
U.S. Appl. No. 15/677,227, Non-Final Office Action, dated Jun. 13, 2019, 10 pgs.
U.S. Appl. No. 15/642,919, Final Office Action dated Oct. 28, 2020, 21 pgs.

* cited by examiner

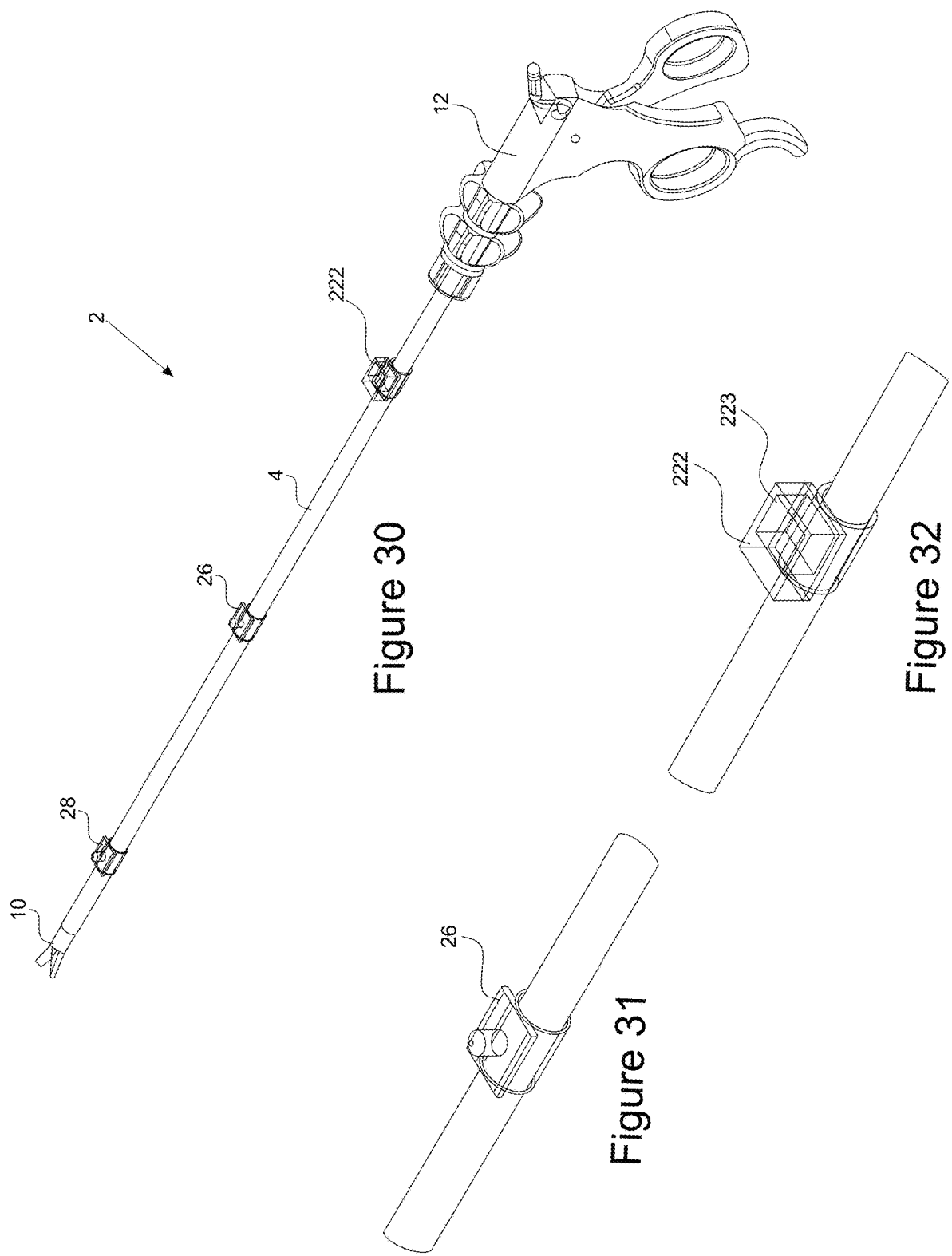

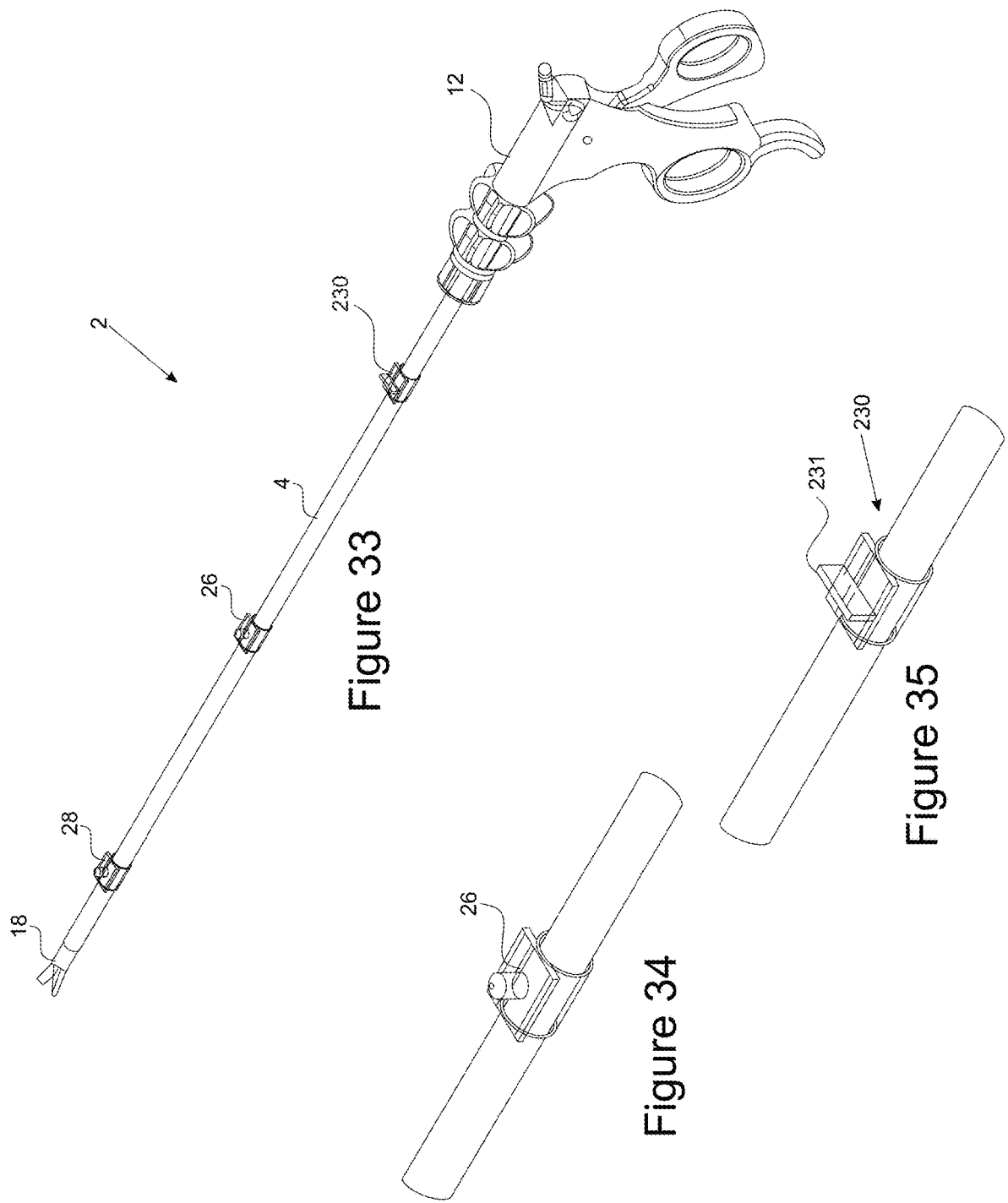

CLAMP INSTALLATION TOOL

RELATED APPLICATION

This application claims the benefit of and priority from U.S. Provisional Patent Application Ser. No. 62/536,364, filed Jul. 24, 2017, entitled "IMPROVED CLAMP INSTALLATION TOOL" and naming C. Kenneth French as an inventor, the entirety of which is incorporated herein by reference for all purposes.

FIELD

The present disclosure relates to surgical clamps and surgical clamp installation tools.

BACKGROUND

The statements in this section merely provide background information related to the present disclosure and may not constitute prior art.

Recently, there has been increased interest in employing surgical clamps to partition sections of a stomach. An example of a bariatric surgical clamp can be found in Jacobs et al., U.S. Pat. No. 8,920,305 (U.S. patent application Ser. No. 11/984,452), Jacobs et al., U.S. patent application Ser. No. 11/797,537 and Jacobs et al., U.S. Pat. No. 8,529,585 (U. S. patent application Ser. No. 13/017,666). The aforementioned patents/patent applications are incorporated by reference herein in their entirety for any purpose. In various instances, there is a need for a tool to install surgical clamps to partition sections of a stomach.

SUMMARY

A clamp installation tool is provided. The clamp installation tool may have a longitudinal main body with an elongate member having a longitudinal support platform configured to support a clamp. The clamp installation tool may have a selectable retention mechanism with a plurality of bosses configured to be received into corresponding apertures of the clamp. The clamp installation tool may have a tip manipulation member coupled to a distal end of the longitudinal main body and arcuately articulable relative to the longitudinal main body.

Referring now to further example embodiments of the clamp installation tool, the clamp installation tool may include wherein the longitudinal main body is made of plastic. In various embodiments, the tool is a single-use tool. In various embodiments, the tool is reusable. The clamp installation tool may also have a sealing channel including a cylindrical tube receivable over the clamp installation tool and insertable into a trocar.

The selectable retention mechanism having a plurality of bosses may also include a distal boss extending from the longitudinal main body at a position closer to the tip manipulation member than an intermediate boss, and the intermediate boss extending from the longitudinal main body at a position farther from the tip manipulation member than the distal boss.

The longitudinal main body may also include a control rod channel configured to receive a control rod extending through the longitudinal main body and connecting the tip manipulation member to a control aspect and a main body attachment mechanism configured to attach to the tip manipulation member.

The main body attachment mechanism may include a cantilevered boss extending from the longitudinal main body, a first main body side flange and a second main body side flange extending from the cantilevered boss and defining a main body flange channel disposed between the first main body side flange and the second main body side flange, and a retention pin configured to retain the tip articulation member in attachment to the main body attachment mechanism.

The tip manipulation member may include a manipulation member main body extending outwardly from an attachment mechanism configured to connect to the main body attachment mechanism, and a retention hook extending from the manipulation member main body and configured to receive a tip retention aperture of a clamp.

The tip manipulation member may include an attachment mechanism having a first side flange and a second side flange extending outwardly from the manipulation member main body and spaced apart to provide a flange channel, an attachment mechanism flange web connecting the first side flange and the second side flange, a retention aperture disposed through the first side flange and the second side flange and configured to receive the retention pin of the main body attachment mechanism to permit articulation of the tip manipulation member about an axis provided by the retention pin and along an articulation path, and an offset articulation aperture spaced an articulation offset radius from the retention aperture and configured to connect to the control rod.

The tip manipulation member may include an angled tip including a safety dome at the outermost distal end of the tip manipulation member, the safety dome including a half-hemisphere.

A further clamp installation tool is provided. The further clamp installation tool may have a longitudinal main body with an elongate member having a longitudinal support platform configured to support a clamp, a selectable retention mechanism configured to connect to the clamp, and a tip manipulation member coupled to a distal end of the longitudinal main body and arcuately articulable relative to the longitudinal main body.

In various embodiments, a clamp installation tool may also include a control aspect configured to articulate the tip manipulation member. The control aspect may have a single use grip including an actuator configured to articulate the tip manipulation member, and a safety configured to inhibit operation of the actuator.

Moreover, the selectable retention member may also include an end point ramp configured to receive an aft end retention nub of the clamp. The selectable retention mechanism may include an aft nub capture boss having a clamp receiving passage configured to receive an aft end retention nub of the clamp. The selectable retention mechanism may have a lateral reaction plate including a reaction wall configured to press against an aft end retention nub of the clamp.

A method of bariatric clamp installation using a clamp installation tool is provided. The method may include connecting a distal retention aperture of a clamp to a distal boss of a selectable retention mechanism of the clamp installation tool, connecting an intermediate retention aperture of the clamp to an intermediate boss of the selectable retention mechanism of the clamp installation tool, and connecting a tip retention aperture of the clamp to a retention hook of a tip manipulation member of the clamp installation tool. In various instances, the clamp installation tool is configured in a coaxial configuration wherein the tip manipulation member is at least partially coaxial with a longitudinal main body of the clamp installation tool. The method may also include inserting the clamp installation tool through an incision and proximate to an organ to be clamped, actuating the clamp installation tool by a control aspect to an actuated configuration wherein the tip manipulation member is not at least partially coaxial with the longitudinal main body of the clamp installation tool, and grasping the clamp proximate to the tip retention aperture and selectably disconnecting the tip retention aperture from the clamp installation tool. The method may further include actuating the clamp installation tool by the control aspect to the coaxial configuration, and retracting the clamp installation tool from the body cavity leaving the clamp emplaced within the body cavity.

The method may further include inserting the clamp installation tool through a sealing channel having a cylindrical tube receivable over the clamp installation tool and insertable into a trocar within the incision, and inserting the combination of the sealing channel disposed over the clamp installation tool into the trocar.

Further embodiments and apparatuses, including other areas of applicability, will become apparent from the description provided herein. It should be understood that the description and specific examples are intended for purposes of illustration only and are not intended to limit the scope of the present disclosure in any manner.

BRIEF DESCRIPTION OF THE DRAWINGS

For a more complete understanding of various embodiments of the present invention and the advantages thereof, reference is now made to the following brief description, taken in connection with the accompanying drawings and detailed description, wherein like reference numerals represent like parts, and in which:

FIGS. 30-32 depict views of another example embodiment of a clamp installation tool having a selectable retention mechanism with an aft nub capture boss;

FIGS. 33-35 depict views of another example embodiment of a clamp installation tool having a selectable retention mechanism with an aft lateral reaction plate.

DETAILED DESCRIPTION

Figure 1:
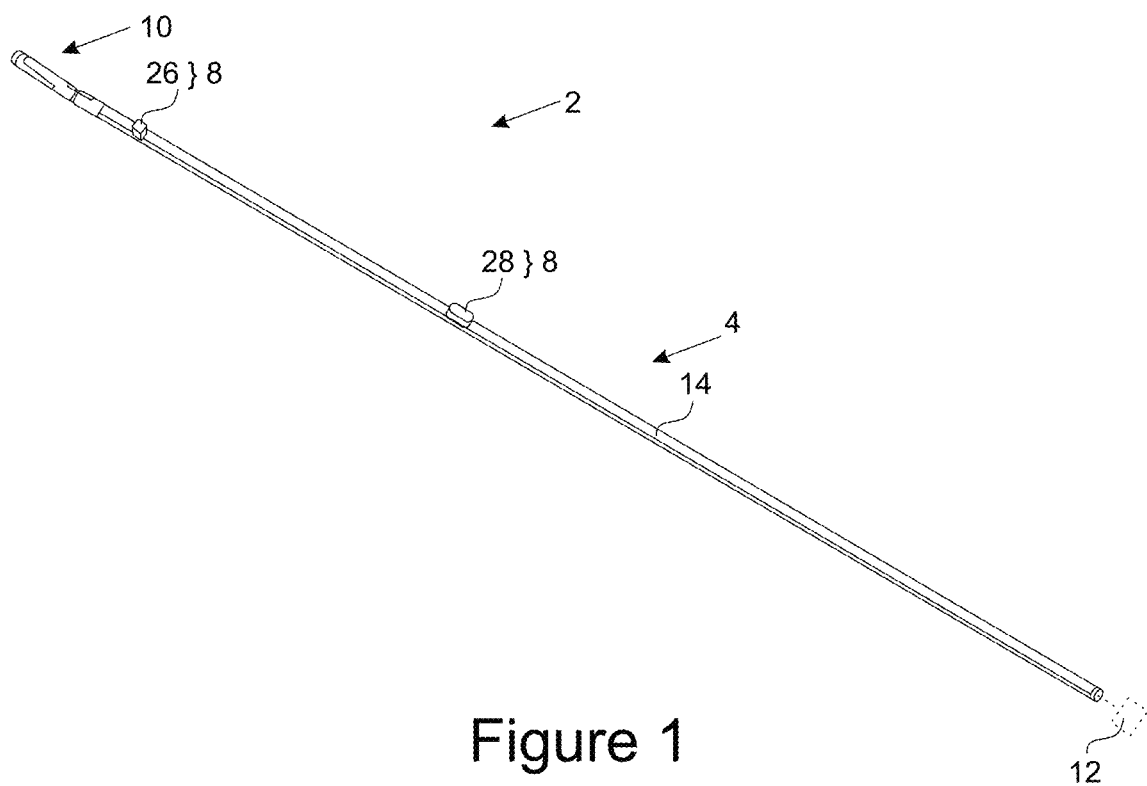
FIG. 1 is a view of an example embodiment of aspects of a clamp installation tool.

The following description is merely exemplary in nature and is not intended to limit the present disclosure, application, or uses. It should be understood at the outset that although an exemplary implementation of the present invention is illustrated below, the present invention may be implemented using any number of techniques, whether currently known or in existence. The present invention should in no way be limited to the exemplary implementations, drawings, and techniques illustrated below, including the exemplary design and implementations illustrated and described herein. Additionally, the drawings contained herein are not necessarily drawn to scale, and may be provided in a variety of different dimensions, shapes and configurations. Any provided dimensions are provided only to illustrate a particular exemplary implementation, and should in no way be construed to limit the present invention absent an explicit recitation of such dimensions and then only with respect to the aspect or aspects reciting the dimension or dimensions.

Referring to FIGS. 1-27, an embodiment of a clamp 88 (also referred to herein as a bariatric clamp 88) engages with an embodiment of a clamp installation tool 2. In various embodiments, the clamp 88 and the clamp installation tool 2 are designed for performing bariatric surgery through a trocar 84. The clamp 88, in one or more embodiment, may be approximately fifteen to thirty centimeters in length to accommodate partitioning of a human stomach. To accommodate insertion through a trocar 84, the closed clamp 88 will preferably have a diameter or circumference less than fifteen millimeters over the entirety of its length or along the majority of its length. A section of the clamp installation tool 2 intended for insertion through the trocar 84 has a similar diameter or a smaller diameter. It is envisioned that other embodiments of the clamp 88 and installation tool can be of other sizes. It is additionally envisioned that the clamp 88 may be articulated in at least one plane to provide different angles and lengths of partition to the stomach. It is also envisioned that other embodiments of the clamp 88 and installation tool can be used for clamping other parts of the human body and/or for clamping other types of bodies or structures. Finally, it should be understood that the clamp installation tool 2 may be used to install embodiments of the surgical clamp 88 other than those explicitly illustrated in the figures.

Some embodiments of the clamp installation tool 2 can be used to install the clamp 88 within an abdominal cavity in order to perform bariatric surgery. In particular, the clamp 88 can be positioned, closed, and latched to partition the stomach into a small vertical portion or pouch and an excluded section. The vertical pouch receives food, but the food is not able to enter the excluded section. Using the clamp installation tool 2 to engage with the clamp 88, the clamp 88 may be installed in a substantially vertical position on the stomach in one embodiment. That is, if the human patient having the clamp 88 installed were to stand upright, the longitudinal axis of the clamp 88 would be substantially parallel to the gravity vector. Thus, a passage forming section formed in the bottom of the stomach by the clamp 88 allows gastric juices to flow from the excluded section into the vertical pouch.

Various embodiments of clamps 88 and systems and methods for installation thereof are taught in U.S. Pat. No. 10,420,664 (U.S. patent application Ser. No. 14/836,621) entitled "Bariatric Clamp with Suture Portions, Magnetic Inserts, and Curvature" and incorporated by reference herein.

A method for clamping an internal organ can include inserting a surgical clamp 88 through an opening into a body of a living organism. Then the two elongated members of the surgical clamp 88 are positioned on opposite sides of an internal organ of the living organism. Closing and latching the surgical clamp 88 to partition a cavity inside the internal organ includes clamping the exterior of the internal organ with the two elongated members.

As mentioned above, the internal organ can be a human stomach. In this case, closing and latching the clamp 88 can include installing the clamp 88 in a substantially vertical or angled position with a passage forming section of the clamp 88 located towards a bottom of the stomach. This positioning can create a small, vertical stomach pouch and thereby limit the intake of food into an excluded section or portion of the stomach, but still allow gastric juices from the excluded portion of the stomach to flow into the vertical stomach pouch. This partitioning can alter the production of hormones, enzymes and chemicals that affect metabolism, energy levels, hunger, digestion, and absorption of nutrients that are affected by exclusion of gastric fundus and body of the stomach by the partitioning. Sheathing aspects of clamp 88 in silicone padding material may reduce trauma and/or necrosis of the stomach or other internal organ and enable successful reversal of the surgery. Thus, the method can further include reversing the surgery by removing the clamp 88.

Inserting the surgical clamp 88 can include performing natural orifice transluminal endoscopic surgery (NOTES). Alternatively, or additionally, it can include performing a combination of NOTES and an assistant trocar placed into an abdominal cavity. This combination can include two or more of a conventional, laparoscopic, NOTES, and one port technique. The NOTES technique can include at least one of transgastric, transvaginal, transrectal, transcolonic, or combinations thereof. The one port technique is used for the introduction of several instruments, and encompasses a one port abdominal (including umbilical), perineal, retroperitoneal approaches, or combinations thereof.

A method for clamping an internal organ can include engaging a surgical clamp 88 to a clamp installation tool 2. The surgical clamp 88 installation tool can be employed to insert the clamp 88 through an opening in a body cavity of a living organism. Then the tool can be employed to position the clamp 88 on opposite sides of an internal organ within the body cavity. The clamp 88 can be latched to fix it in position to partition the internal organ and the cavity inside the internal organ. The clamp 88 can be disengaged from the clamp installation tool 2, and the tool can be retracted from the body cavity. Moreover, additional steps may be employed to secure the clamp 88 in place, such as using sutures.

With reference now to FIGS. 1-20, a clamp installation tool 2 is provided. A clamp installation tool 2 may be configured to facilitate the insertion of a clamp 88 through a trocar 84 and into a body cavity for clamping a bodily organ. In various instances, a sealing channel 86 is further provided. For instance, the sealing channel 86 may enhance the fluidic sealing of the body cavity from the external environment as the clamp installation tool 2 penetrates through the trocar 84 to emplace the clamp 88.

In various instances, a clamp installation tool 2 may be reusable. For instance, a clamp installation tool 2 may be used repeatedly during multiple procedures. As such, the articulating aspects of the clamp installation tool 2 (discussed elsewhere herein) may be repeatedly articulable. In further instances, a clamp installation tool 2 may be a single-use tool. In various instances, the articulating aspects of the single-use clamp installation tool 2 may not be repeatedly articulable, or may be formed of material having less resiliency than the reusable clamp installation tool 2.

A clamp installation tool 2 may have a longitudinal main body 4. The longitudinal main body 4 may provide a primary support of the clamp installation tool 2. In various instances, the longitudinal main body 4 comprises an elongate member, for instance, a relatively long and slender member shaped to be insertable through a trocar 84. The longitudinal main body 4 may support a selectable retention mechanism 8.

A selectable retention mechanism 8 may comprise an aspect extending from the longitudinal main body 4 and configured to selectably connect to and disconnect from a clamp 88. The selectable retention mechanism 8 may be engaged to a clamp 88 for insertion of the clamp 88 through a trocar 84 and positioning of the clamp 88 inside the body. Thereafter, all or part of the selectable retention mechanism 8 may be selectably disengaged from the clamp 88 in order to emplace different aspects of the clamp 88 in position relative to an organ to be clamped. The selectable retention mechanism 8 may comprise a plurality of bosses configured to be received into corresponding apertures of a clamp. In this manner, the selectable retention mechanism 8 is said to be "selectable."

The longitudinal main body 4 may support a tip manipulation member 10. A tip manipulation member 10 may comprise a member coupled to the longitudinal main body 4, for instance, at a distal end of the longitudinal main body 4. The tip manipulation member 10 may be articulable relative to the longitudinal main body 4 in at least one plane of motion. The tip manipulation member 10 may be attached to a distal end of the longitudinal main body 4 and rotatable about the point of attachment in the same plane in which the longitudinal main body 4 lies (i.e., arcuately articulable relative to the longitudinal main body 4). For instance, the tip manipulation member 10 may be movable between different positions. For instance, the tip manipulation member 10 may be movable from being aligned co-axially with the longitudinal main body 4 so that longitudinal axes of each are coincident and parallel, to being aligned at an angle relative to the longitudinal main body 4, so that the longitudinal axes of each are at an angle, for instance, intersecting at a point and extending at an acute angle relative to one another, or a right angle, or an obtuse angle, or another angle as desired. In various instances, the tip manipulation member 10 is articulable from being aligned with the longitudinal main body 4 and being at a right angle to the longitudinal main body 4.

Figure 36:
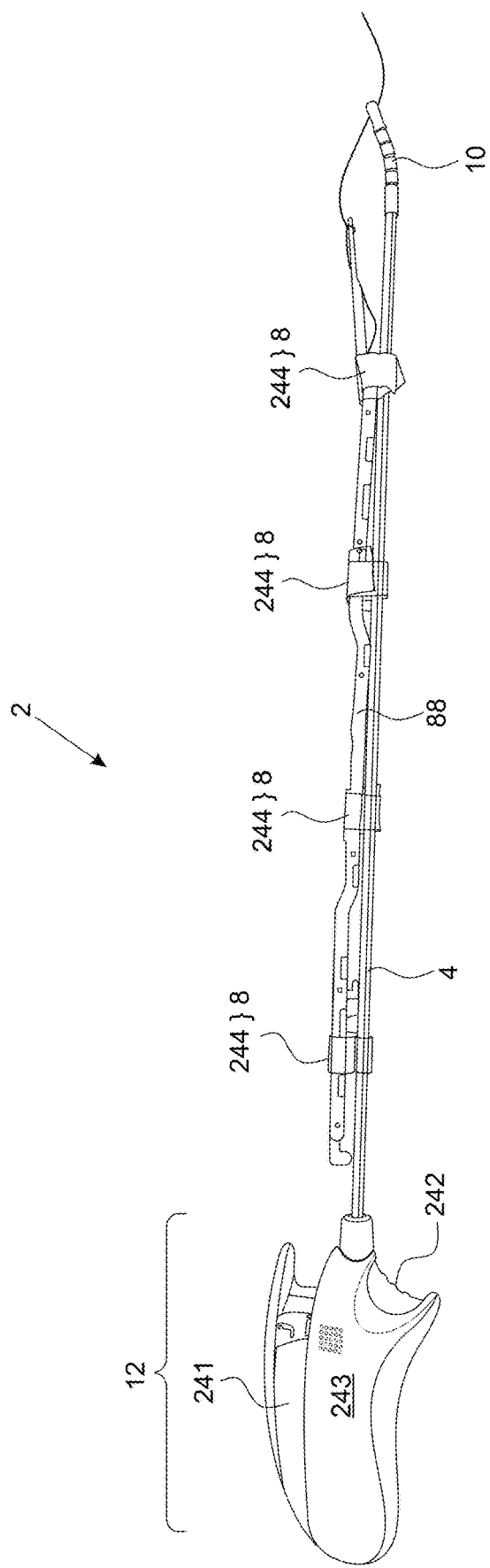
FIGS. 36-37 depict views of an example embodiment of a clamp installation tool having a single use grip.
Figure 37:
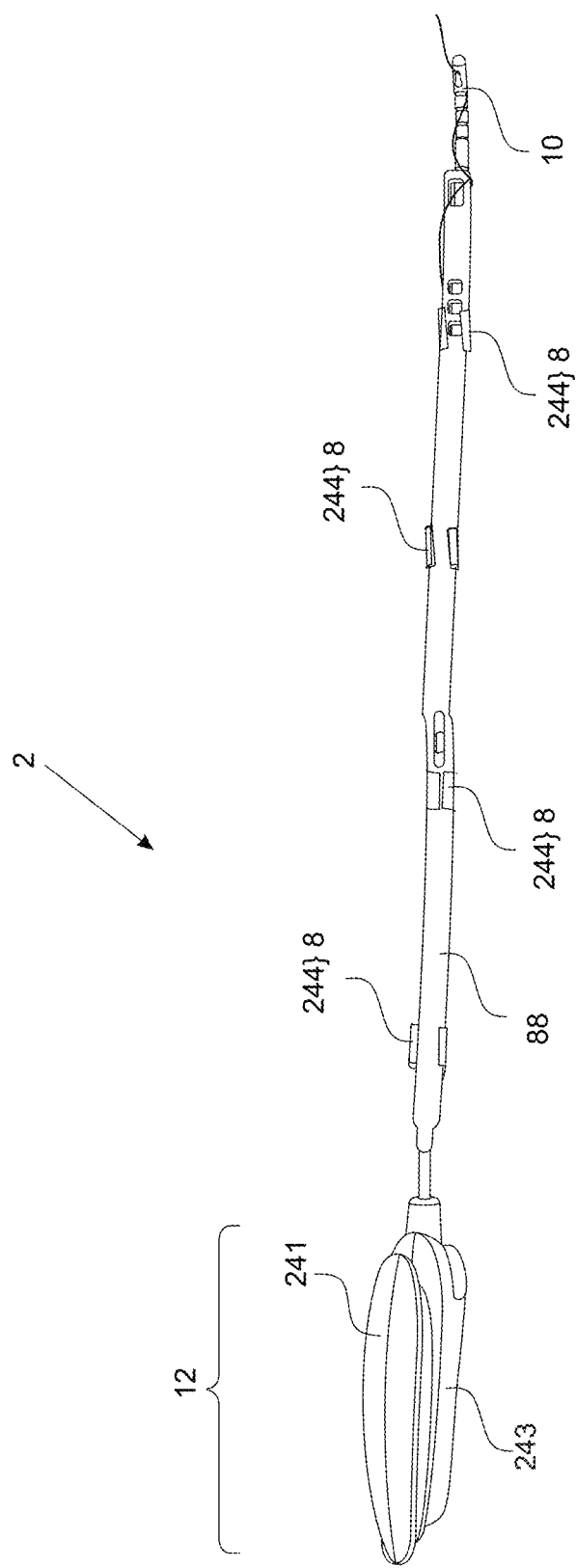

The longitudinal main body 4 may support a control aspect 12. For example, a control aspect 12 may provide a mechanism whereby an operator may grip the clamp installation tool 2 and/or may control the articulation of the tip manipulation member 10. In various instances, the control aspect 12 comprises scissor-style grips, although in further instances, different configurations are contemplated. The control aspect 12 may be coupled to the longitudinal main body 4, for instance, at a distal end of the longitudinal main body 4, such as an opposite distal end relative to the tip manipulation member 10. With momentary reference to FIGS. 36-37, the control aspect 12 may comprise a single use grip 243 for a clamp installation tool 2 designed to be used a limited number of times, for instance, once. The single use grip 243 may comprise a plastic grip, for instance, a molded plastic grip. The single use grip 243 may further comprise an actuator 241 comprising a squeezable aspect articulable by an operator by squeezing of the operator's hand. The single use grip 243 may further comprise a safety 242 configured to selectably inhibit or allow operation of the actuator 241. In various instances, the orientation of the safety 242 and actuator 241 may be as depicted in FIG. 36-37, although in further instances, they may be reversed so that the actuator 241 is operated by an index finger and the safety 242 operated by a gripping action.

With specific reference now to FIGS. 1, 2, 8, 9, and 13, 22, 24, 26, 29-37, the longitudinal main body 4 may have further aspects. For example, the longitudinal main body 4 may comprise a longitudinal support platform 14 (FIGS. 1, 2, 8, 9, 13). A longitudinal support platform 14 may comprise a surface of the longitudinal main body 4 extending parallel to a longitudinal axis of the longitudinal main body 4, such as extending along the length of the longitudinal main body 4. The longitudinal support platform 14 comprises a surface of the longitudinal main body 4 shaped to provide support to a clamp 88 when the clamp 88 is emplaced on the clamp installation tool 2. In various instances, the longitudinal support platform 14 comprises a planar surface. For example, a longitudinal main body 4 may comprise a generally cylindrical member, whereas the longitudinal support platform 14 comprises an area of flattening of the generally cylindrical member. As such, a clamp installation tool 2 may comprise a longitudinal main body 4 comprising a partial cylinder whereas the longitudinal support platform 14 may comprise a planar platform with lateral edges coinciding with the endpoints of line tracing the circumferential arc of the profile of the longitudinal main body 4. In further embodiments, such as wherein the longitudinal main body 4 comprises a flat bar member having a rectangular profile, the longitudinal support platform 14 may comprises a side of the longitudinal main body 4. In yet further embodiments, such as wherein the longitudinal main body 4 comprises an oval member having an oval profile, the longitudinal support platform 14 may be non-planar, such as having a curved shape.

Figure 3:
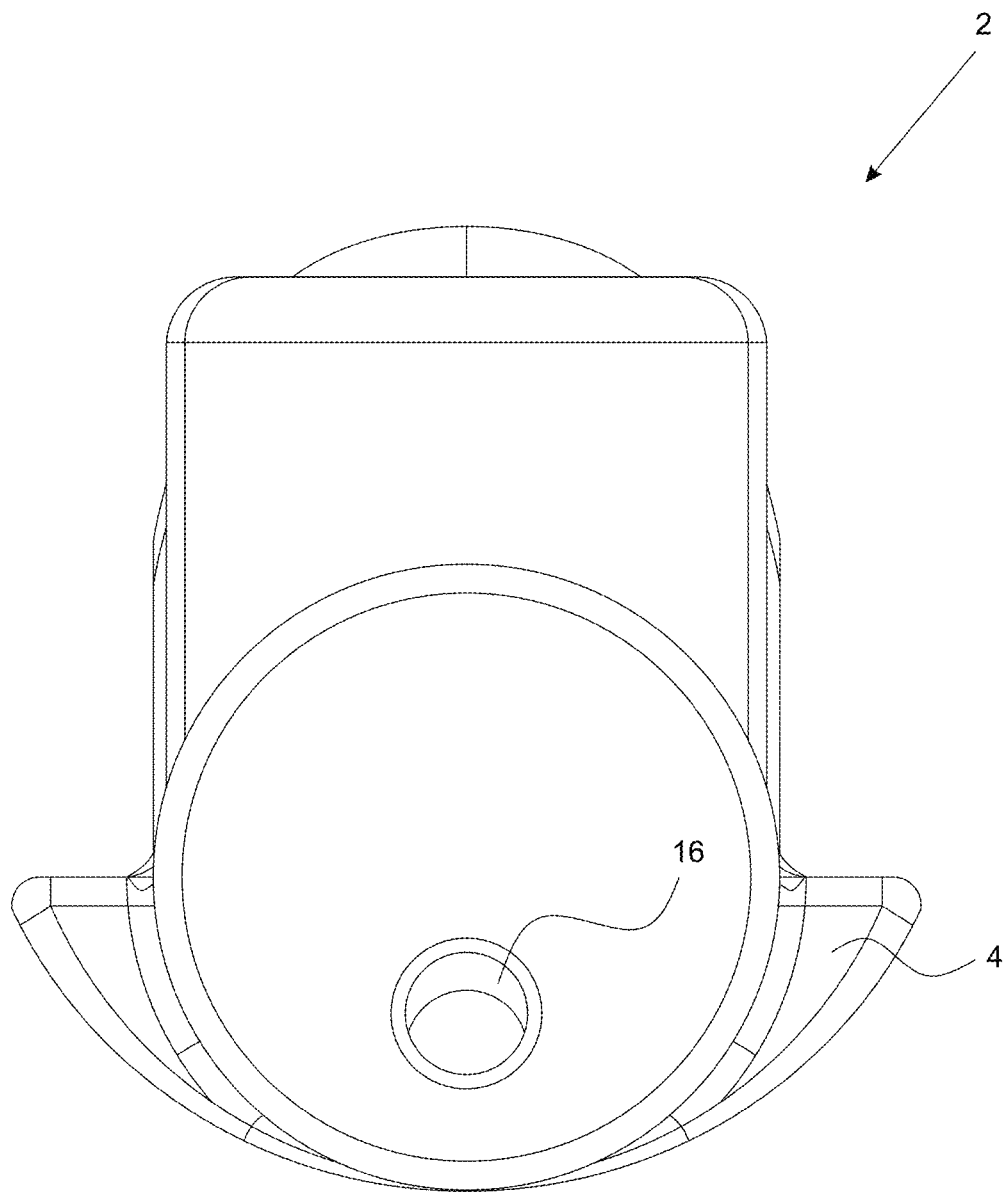
FIG. 3 is a second end view of an example embodiment of aspects of a clamp installation tool showing an opposite end of the clamp installation tool of FIG. 2.
Figure 8:
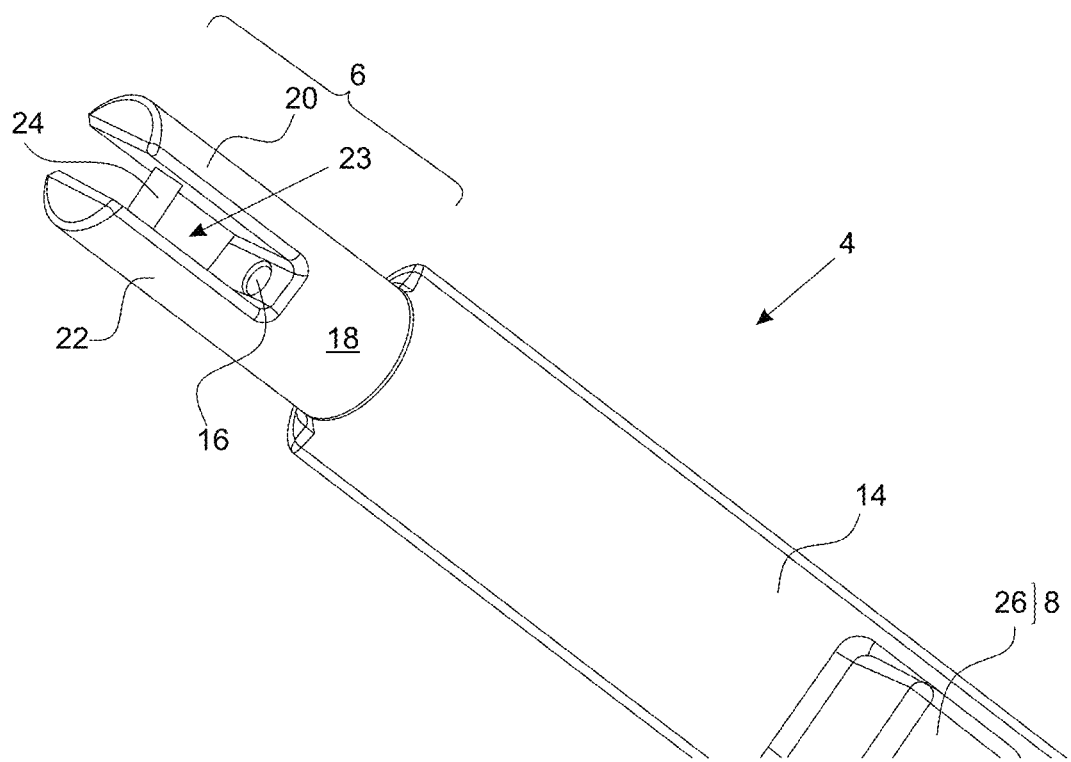
FIG. 8 is an isometric view of an aspect of a longitudinal main body of a clamp installation tool configured to mechanically connect to a tip manipulation member of a clamp installation tool.

The longitudinal main body 4 may comprise a control rod channel 16, such as that shown in FIGS. 3 and 8. A control rod channel 16 may comprise an internal passage of the longitudinal main body 4 configured to guide a control rod and/or cable from the control aspect 12 to the tip manipulation member 10 to facilitate movement of the tip manipulation member 10 in response to operation of the control aspect 12. In various instances, the control rod channel 16 comprises a cylindrical channel defined through the longitudinal main body 4 from apertures at each distal end of the longitudinal main body 4, although in further instances, the control rod channel 16 may comprise a rectangular channel, or an oval channel, or an irregularly shaped channel, or a keyed channel, or any shape channel as desired.

The longitudinal main body 4 may comprise a main body attachment mechanism 6 such as that shown in FIGS. 1, 8-10, and 18. A main body attachment mechanism 6 comprises a mechanical connection between the longitudinal main body 4 and the tip manipulation member 10. The main body attachment mechanism 6 comprises a mechanical connection configured to retain the tip manipulation member 10 to the distal end of the longitudinal main body 4 and permit articulation of the tip manipulation member 10 relative to the longitudinal main body 4, for instance, permitting arcuate motion about an axis of rotation proximate to the distal end of the longitudinal main body 4 and proximate to a distal end of the tip manipulation member 10.

With reference to FIGS. 1, 9, 10, and 17 as well as 22, 26, 29-37, and having discussed specific aspects of the longitudinal main body 4, attention is now directed to specific aspects of the selectable retention mechanism 8. A selectable retention mechanism 8 may comprise one or more bosses extending outward away from the longitudinal main body 4 and configured to be received into an aspect of the clamp 88 to retain the clamp 88 in selectable mechanical communication with the longitudinal main body 4. Alternatively, a selectable retention mechanism 8 may comprise one or more apertures extending into the longitudinal main body 4 and configured to receive an aspect of the clamp 88 to retain the clamp 88 in selectable mechanical communication with the longitudinal main body 4.

The selectable retention mechanism 8 may comprise bosses extending in a direction normal to the plane of the longitudinal support platform 14. In instances in which the longitudinal support platform 14 is non-planar, the selectable retention mechanism 8 may comprise bosses extending in a direction normal to a tangent of the longitudinal support platform 14. In various embodiments, the selectable retention mechanism 8 may comprise bosses extending radially outward with respect to the longitudinal main body 4.

Yet furthermore, the selectable retention mechanism 8 may comprise one or more bosses with apertures therein and in yet further instances may include one or more plates extending in a direction normal to a tangent of the longitudinal support platform and oriented laterally (e.g., generally perpendicular to the longitudinal axis of the longitudinal main body).

The selectable retention mechanism 8 may comprise an intermediate boss 26 and a distal boss 28. The intermediate boss 26 may comprise a trapezoidal boss. For instance, the intermediate boss 26 may comprise a rectangular boss. In further instances, the intermediate boss 26 may comprise a square boss, or a cylindrical boss, or an arbitrarily shaped boss, or any shape as desired. The intermediate boss 26 may comprise a boss formed to have a shape corresponding to an aperture of the clamp 88 and configured to be received by the aperture of the clamp 88. The intermediate boss 26 may be located between a distal boss 28 and the control aspect 12 (FIGS. 1, 9, 10) of the clamp installation tool 2.

The distal boss 28 may comprise a trapezoidal boss. For instance, the distal boss 28 may comprise a square boss. In further instances, the distal boss 28 may comprise a rectangular boss, or a cylindrical boss, or an arbitrarily shaped boss, or any shape as desired. The distal boss 28 may comprise a boss shaped to have a shape corresponding to an aperture of the clamp 88 and configured to be received by the aperture of the clamp 88. The distal boss 28 may be located between an intermediate boss 26 of the selectable retention mechanism 8 and the tip manipulation member 10 (FIGS. 1, 2, 4, 5, 6, 7, 9, 10, 16, and 20) of the clamp installation tool 2. The distal boss 28 may be smaller than the intermediate boss 26, though each boss may be any size as desired to correspond to aspects of the clamp 88 (FIGS. 9-15, 17-20).

With particular emphasis on FIGS. 25-29, the selectable retention mechanism 8 may comprise an end point ramp 200. An end point ramp may comprise a boss located closest to a control aspect 12. In various instances, the intermediate boss 26 and distal boss 28 are omitted and the end point ramp 200 connects to one end of a clamp 88 and the tip manipulation member 10 connects to the other end of the clamp 88.

With particular emphasis on FIGS. 30-32, in various instances the selectable retention mechanism 8 may comprise an aft nub capture boss 222. An aft nub capture boss 222 may comprise a boss, such as a trapezoidal boss, having an opening disposed therein and shaped to receive an aspect of a clamp 88 into the opening. For example, an aft nub capture boss 222 may comprise a clamp receiving passage 223 configured to receive a projection from a clamp 88 extending generally normal to a surface of the clamp 88 to retain an end of the clamp 88 in connection to the aft nub capture boss 222 while the clamp 88 is stretched along the longitudinal main body 4.

With particular emphasis on FIGS. 33-35, in various instances the selectable retention mechanism 8 may comprise an aft lateral reaction plate 230. An aft lateral reaction plate 230 may comprise a reaction wall 231 extending in a direction normal to a tangent of the longitudinal support platform 14 and oriented laterally to the longitudinal main axis of the longitudinal main body 4, so as to retain an end of the clamp 88 in connection to the reaction wall 231 while the clamp 88 is stretched along the longitudinal main body 4. For example, the reaction wall 231 may press against an aft end retention nub 202 of a clamp 88.

With particular emphasis on FIGS. 36-37, the selectable retention mechanism 8 may comprise one or more clip 244. A clip 244 may comprise an structure projecting outwardly from the longitudinal main body 4 and defining an aperture to selectably retain the clamp 88 proximate to the longitudinal main body 4, and yet also release the clamp 88 in response to a releasing force. For instance, the clip 244 may comprise two curved aspects partially enclosing the clamp 88 and springable to permit the clamp to pass through a space of the clip 244.

Turning now to FIGS. 25, 26, and 28-32, the selectable retention mechanism 8 may comprise an end point ramp 200. In various instances the intermediate boss 26 (FIG. 1, 9, 10, 17) and distal boss 28 (FIG. 1, 9, 10) are omitted in lieu of the end point ramp 200. The end point ramp 200 connects to one end of a clamp 88 and the tip manipulation member 10 connects to the other end of the clamp 88. An end point ramp may be configured to receive an aspect of a clamp 88, for instance, an aspect of an end of the clamp 88 such as an aft end retention nub 202. In various instances, the end point ramp 200 comprises an aft removal slide 206. An aft removal slide 206 may comprise an inclined plane surface of the end point ramp 200 extending outwardly from the longitudinal main body 4 and terminating at one end closest the control aspect 12 (FIGS. 1, 9, 10, 29-37) in connection to the longitudinal main body 4 and terminating at another end closest the tip manipulation member 10 (FIGS. 1, 2, 4-7, 9, 10, 16, 20, 22, 23, 26-27, 39, 30-37) at a forward face 220. The forward face 220 may thusly extend radially and/or normally outward from the longitudinal main body 4. Extending between an edge of the aft removal slide 206 and the longitudinal main body 4 may be a first lateral wall 208. Similarly, extending between an opposite edge of the aft removal slide 206 and the longitudinal main body 4 may be a second lateral wall 210. The first lateral wall 208 and second lateral wall 210 may provide structural support and rigidity to the end point ramp 200. In various embodiments, a first lateral wall passage 212 comprises an aperture extending through the first lateral wall 208, the aperture lying in a plane parallel the longitudinal axis of the longitudinal main body 4. In various embodiments, a second lateral wall passage 214 comprises an aperture extending through the second lateral wall 210, the aperture laying in a plane parallel the longitudinal axis of the longitudinal main body 4. A center point of first lateral wall passage 212 and center point of the second lateral wall passage 214 may be coaxially aligned along a shared line perpendicular to the longitudinal main body 4. The aperture of the first lateral wall passage 212 may have an edge aspect 216 comprising a curvature, chamfer, edge radius and or the like. Similarly, the aperture of the second lateral wall passage 214 may have an edge aspect 218 comprising a curvature, chamfer, edge radius and or the like. Finally, a clamp receiving passage 223 may be disposed in a surface of the end point ramp 200, for instance, the aft removal slide 206, and configured to receive the aft end retention nub 202 of the clamp 88 therein. Similarly, the clamp receiving passage 223 may have an edge aspect 221 comprising a curvature, chamfer, edge radius and or the like.

Attention is directed to FIGS. 1, 2, 4, 5, 6, 7, 9, 10, 16, and 20, as well as 22, 24, 26, 27, and 29-37 for a detailed discussion of the tip manipulation member 10. With momentary emphasis on FIG. 5, the tip manipulation member 10 may have a tip manipulation member major longitudinal axis 30. The tip manipulation member major longitudinal axis 30 comprises an axis extending through the tip manipulation member main body 33 (FIG. 5) of the tip manipulation member 10 coincident with its center at all points along the axis.

The tip manipulation member 10 may include a retention hook 32 (FIGS. 4-7, 9-10, 16, 18, 24). The retention hook 32 may comprise a combination of structures and apertures shaped to receive an aspect of the clamp 88. For instance, the clamp 88 may have a tip retention aperture 100 (FIGS. 9, 10, 19, 22, 23) extending through the clamp 88. The retention hook 32 comprises a combination of structures and apertures to selectably connect to the clamp 88 and capable of exerting a tension force on the clamp 88 when the tip manipulation member 10 is in one or more position, such as the coaxial configuration 80 (FIG. 14) of the clamp installation tool 2.

Figure 14:
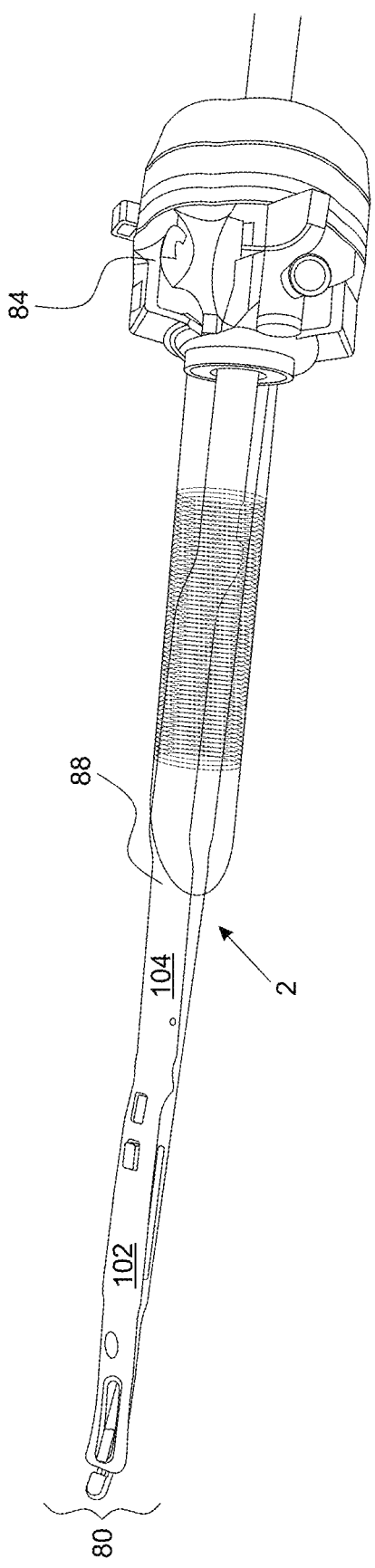
FIG. 14 depicts a clamp installation tool in simulated use with a trocar and inserted into the trocar and with a clamp, wherein the clamp installation tool is in a coaxial configuration.
Figure 15:
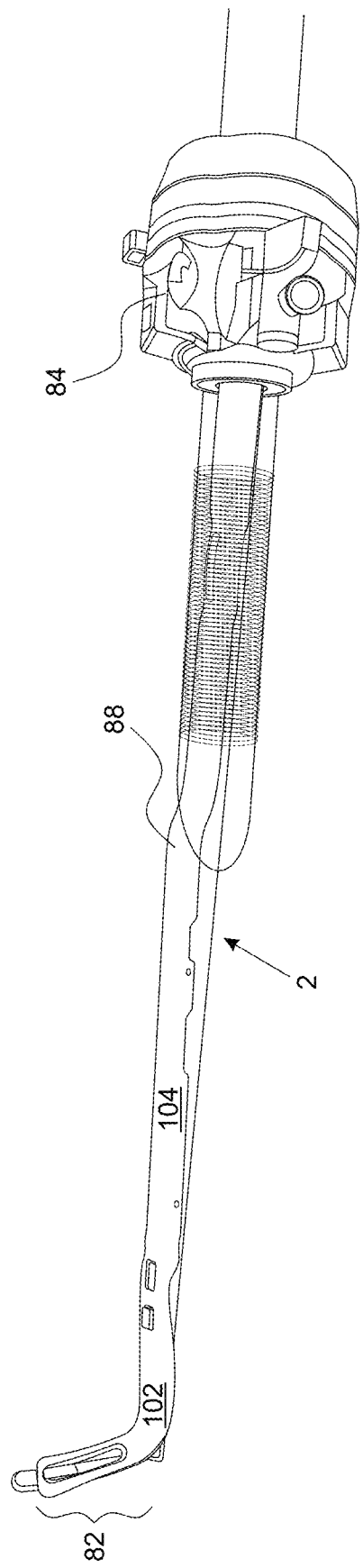
FIG. 15 depicts a clamp installation tool in simulated use with a trocar and inserted into the trocar and with a clamp, wherein the clamp installation tool is in an actuated configuration.
Figure 16:
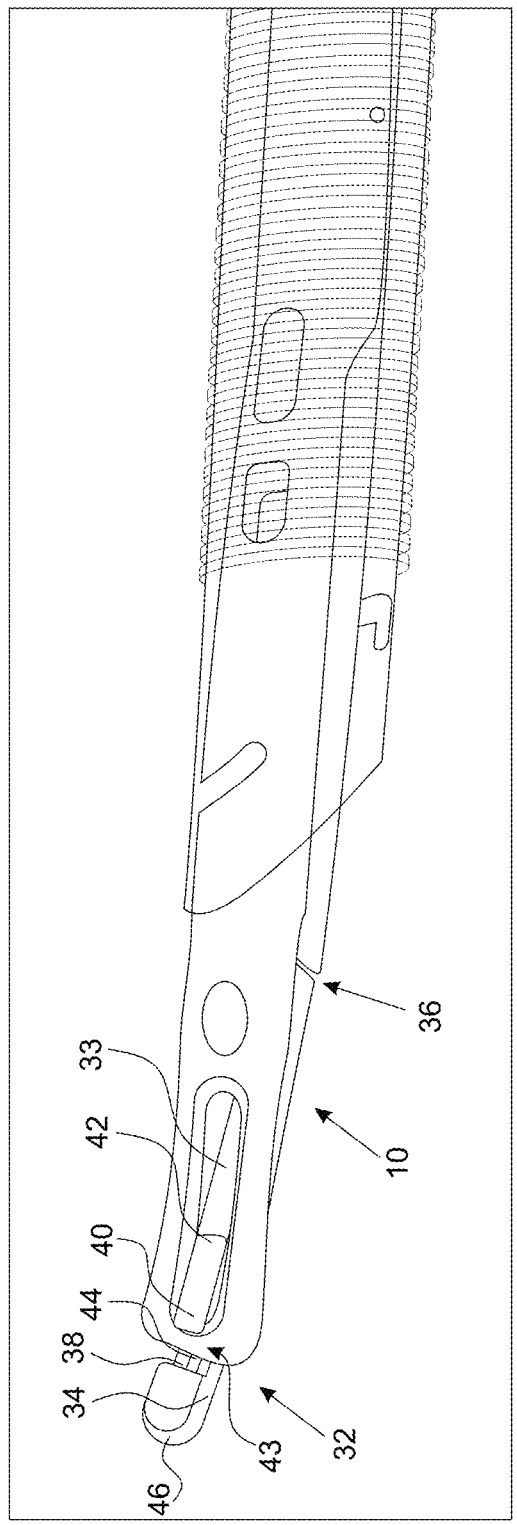
FIG. 16 depicts a close up view of a tip manipulation member of a clamp installation tool in simulated use with a trocar and partially inserted into the trocar, and with a clamp.
Figure 17:
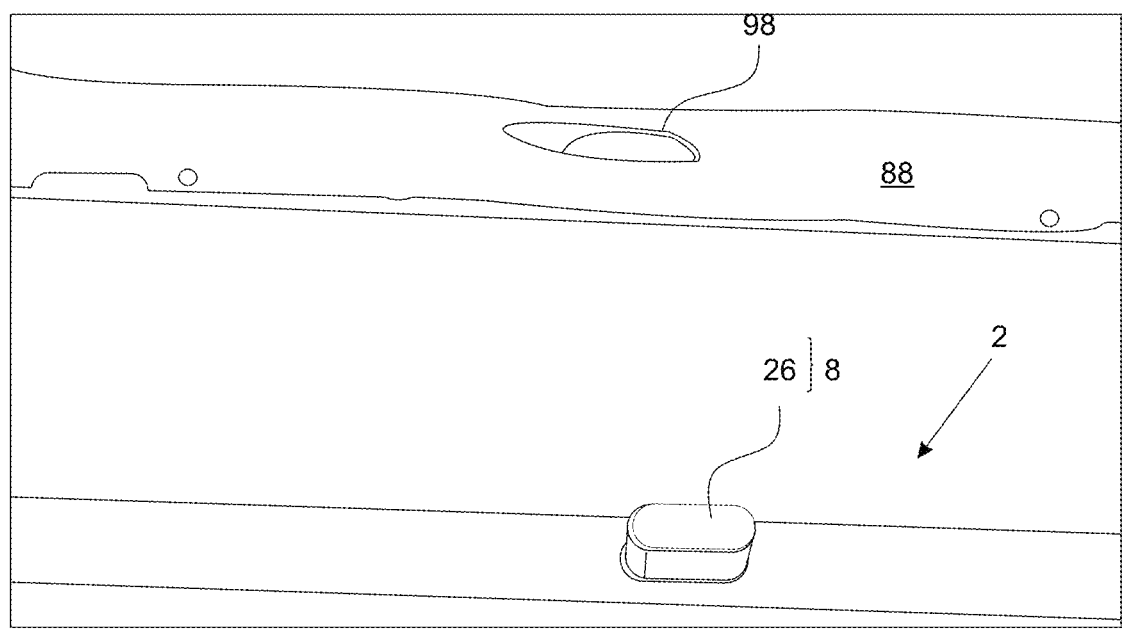
FIG. 17 depicts a close up view of aspects of a selectable retention mechanism of a clamp installation tool with a clamp and without a clamp
Figure 29:
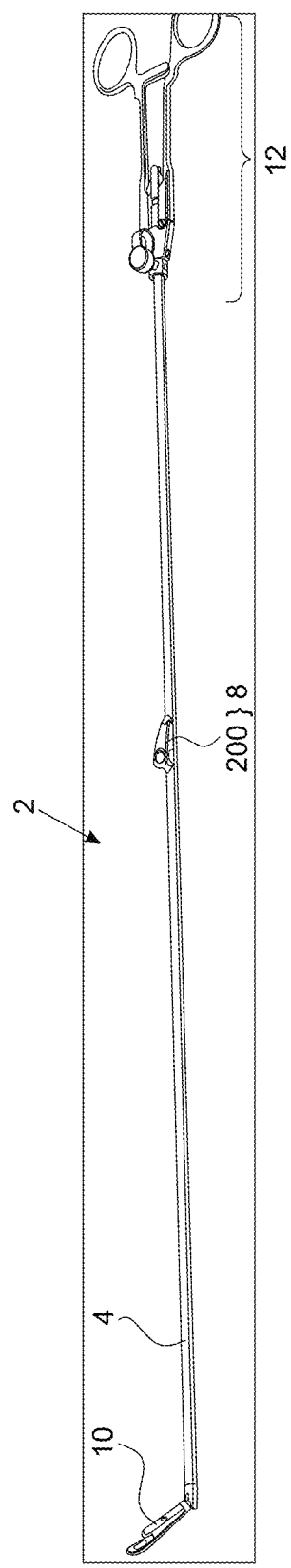
FIG. 29 depicts still yet another view of an example embodiment of aspects of a clamp installation tool having a selectable retention mechanism with an end point ramp and a tip articulation member wherein the clamp installation tool is in an actuated position.

The tip manipulation member 10 may comprise a tip manipulation member main body 33 (FIGS. 4-7, 9-10, 16, 18, 24). The tip manipulation member main body 33 may comprise a cylinder. For example, the tip manipulation member main body 33 may comprise a cylinder of same diameter as the longitudinal main body 4 (FIGS. 1, 2, 3, 8, 9, 10, 13). The tip manipulation member main body 33 may connect the tip manipulation member attachment mechanism 36 (FIGS. 4-7, 10, 16, 18) of the tip manipulation member 10 to the retention hook 32 (FIGS. 4-7, 9, 10, 16, 18, 24) of the tip manipulation member 10. The tip manipulation member main body 33 may provide spacing between the tip manipulation member attachment mechanism 36 (FIGS. 4-7, 10, 16, 18) of the tip manipulation member 10 and the retention hook 32 (FIGS. 4-7, 9, 10, 16, and 18) of the tip manipulation member 10, such that the retention hook 32 (FIGS. 4-7, 9, 10, 16, 18, 24) travels in an arcuate path orbitally relative to the tip manipulation member attachment mechanism 36 as the clamp installation tool 2 changes from a coaxial configuration 80 (FIG. 14) to an actuated configuration 82 (FIGS. 15, 29).

The tip manipulation member 10 may comprise an angled tip 34. The angled tip 34 may comprise a cylinder that is unitary with the tip manipulation member main body 33 and extending outwardly from the tip manipulation member main body 33 at an angle. For example, the angled tip 34 may be at an opposite end of the tip manipulation member main body 33 from the tip manipulation member attachment mechanism 36. The angled tip 34 may form aspects of the retention hook 32, such as bounding one or more aperture configured to receive the clamp 88 in mechanical communication.

Finally, the tip manipulation member 10 may comprise a tip manipulation member attachment mechanism 36 (FIGS. 4-7, 9-10, 16, 18). A tip manipulation member attachment mechanism 36 comprises a structure extending from a distal end of the tip manipulation member main body 33 and joining the tip manipulation member 10 to the longitudinal main body 4 (FIGS. 1-3, 8-10, 13, 22, 24, 26, 29-37) of the clamp installation tool 2. The tip manipulation member attachment mechanism 36 is also configured to interface with the control aspect 12 (FIGS. 1, 9, 10, 29-37) in order to move the tip manipulation member 10 so that the clamp installation tool 2 transitions between a coaxial configuration 80 (FIG. 14) and an actuated configuration 82 (FIGS. 15, 29).

With reference to FIGS. 8-10, and 18, attention is redirected to the main body attachment mechanism 6, and the specific features of the main body attachment mechanism 6 in various example embodiments. For example, a main body attachment mechanism 6 may include a cantilevered boss 18.

A cantilevered boss 18 may comprise a boss extending at least partially coaxially outward from the longitudinal main body 4 at least partially longitudinally. The boss may cantilever from a distal end of the longitudinal main body 4, for instance, the end opposite the control aspect 12 (FIGS. 1, 9, 10, 29-37).

A first main body side flange 20 and a second main body side flange 22 may extend further distally outward from the cantilevered boss 18. The first main body side flange 20 and the second main body side flange 22 may comprise cantilevered flanges extending parallel to one another, such as to receive, or to be received into an aspect of the tip manipulation member 10, such as the tip manipulation member attachment mechanism 36 (FIGS. 4-7, 9-10, 16, 18).

A main body flange channel 23 may comprise a channel defined by the first main body side flange 20 and the second main body side flange 22 between the first main body side flange 20 and the second main body side flange 22. In various embodiments, the tip manipulation member attachment mechanism 36 (FIGS. 4-7, 9-10, 16, 18) has at least one aspect received into the main body flange channel 23.

Finally, the main body attachment mechanism 6 may comprise a retention pin 24 as shown in FIG. 8. The retention pin 24 comprises a shaft extending between the first main body side flange 20 and the second main body side flange 22 through the main body flange channel 23. The retention pin 24 may extend through a corresponding aperture of the tip manipulation member attachment mechanism 36 (FIGS. 4-7, 9-10, 16, 18) of the tip manipulation member 10 (FIGS. 1, 2, 4-7, 9-10, 16, 20, 22, 24, 26, 27, 29, 30-37), so as to maintain mechanical communication of the tip manipulation member 10 and the longitudinal main body 4 and yet permit the rotational movement of the tip manipulation member 10 about an axis provided by the retention pin 24. Thus, the retention pin 24 may comprise an axis of rotation of the tip manipulation member 10 relative to the longitudinal main body 4.

With reference to FIGS. 4-7, 9-10, 16, 18, and 24, the retention hook 32 is now discussed in further detail. In various instances, a retention hook 32 may include a finger aspect 40. A finger aspect 40 may comprise a cantilevered boss extending at least partially collinear with an angled tip minor longitudinal axis 48 (FIGS. 5, 18) of an angled tip 34. In various embodiments, the finger aspect 40 may comprise a cantilevered boss extending at least partially to at least partially enclose a portion of a clamp channel 43 (FIGS. 5, 16, 18, 24) of a retention hook 32. The finger aspect 40 may comprise a member configured to selectably retain a clamp 88 (FIGS. 9-15, 17-20, 22-23, 36-37) in mechanical communication with the tip retention aperture 100 (FIGS. 9, 10,

19, 22, 23) by extending through a tip retention aperture 100 (FIGS. 9, 10, 19, 22, 23) of the clamp 88 (FIGS. 9-15, 17-20, 22-23, 36-37).

Figure 4:
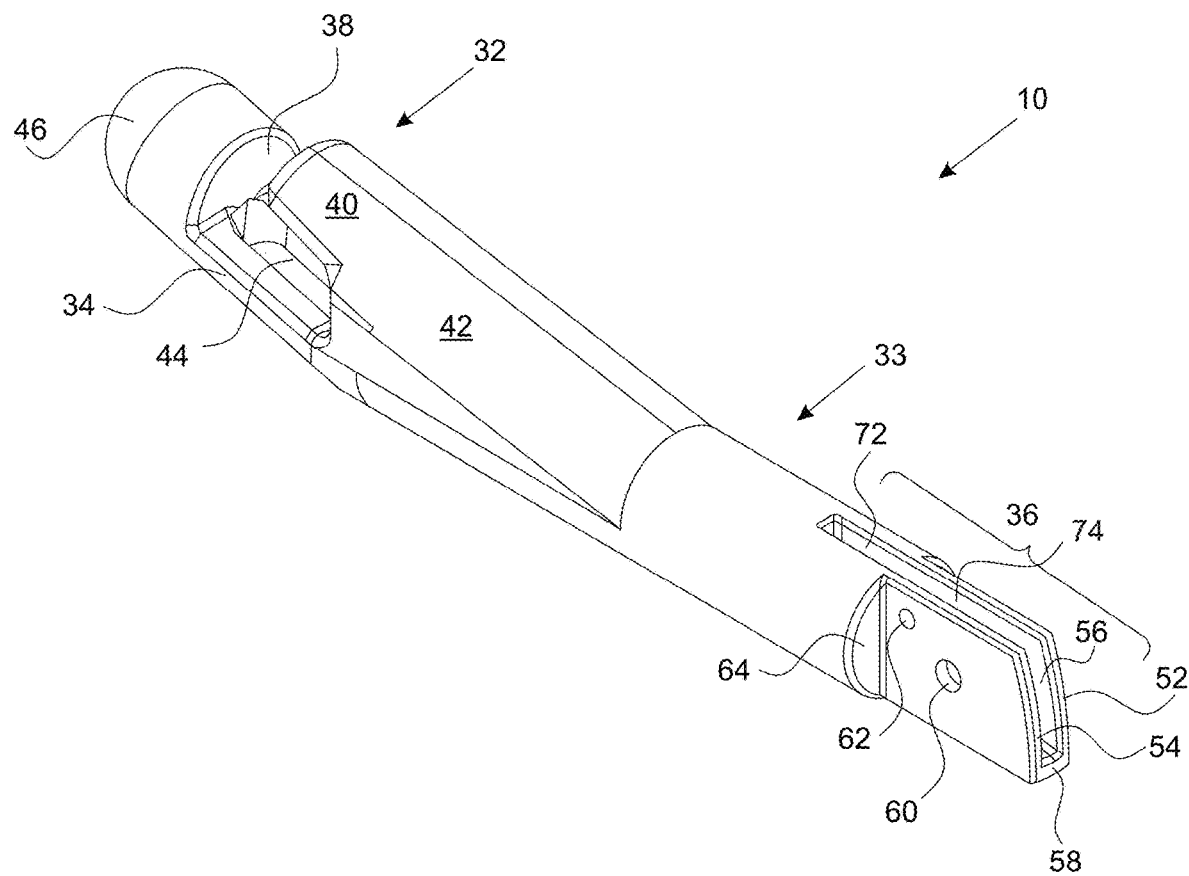
FIG. 4 is an isometric view of a tip manipulation member of a clamp installation tool.
Figure 5:
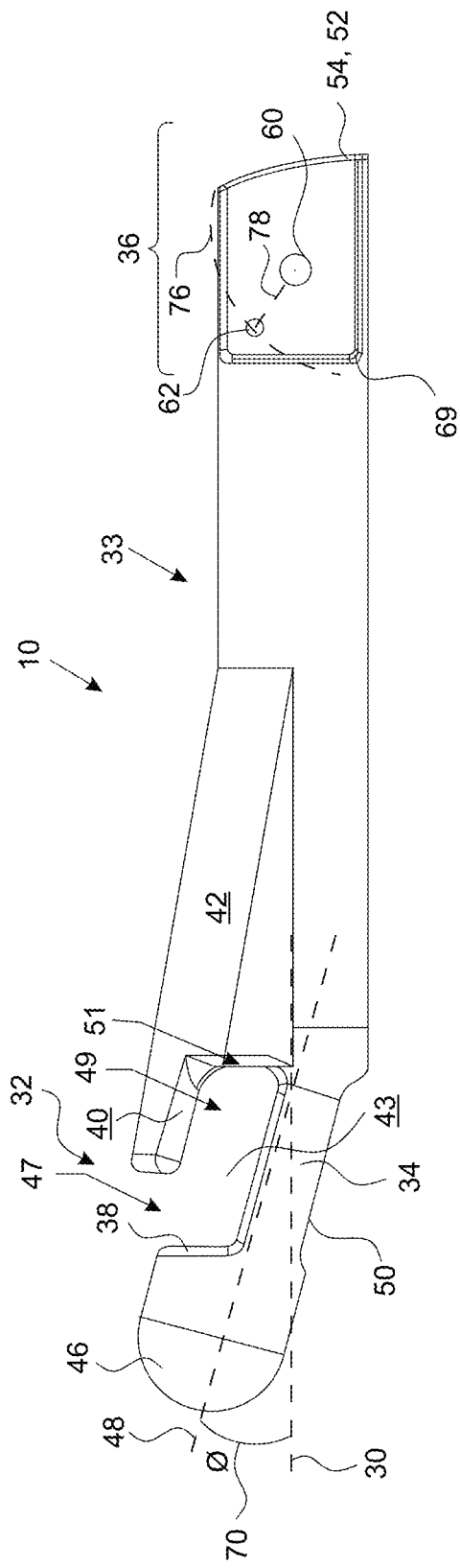
FIG. 5 is a side view of a tip manipulation member of a clamp installation tool.
Figure 18:
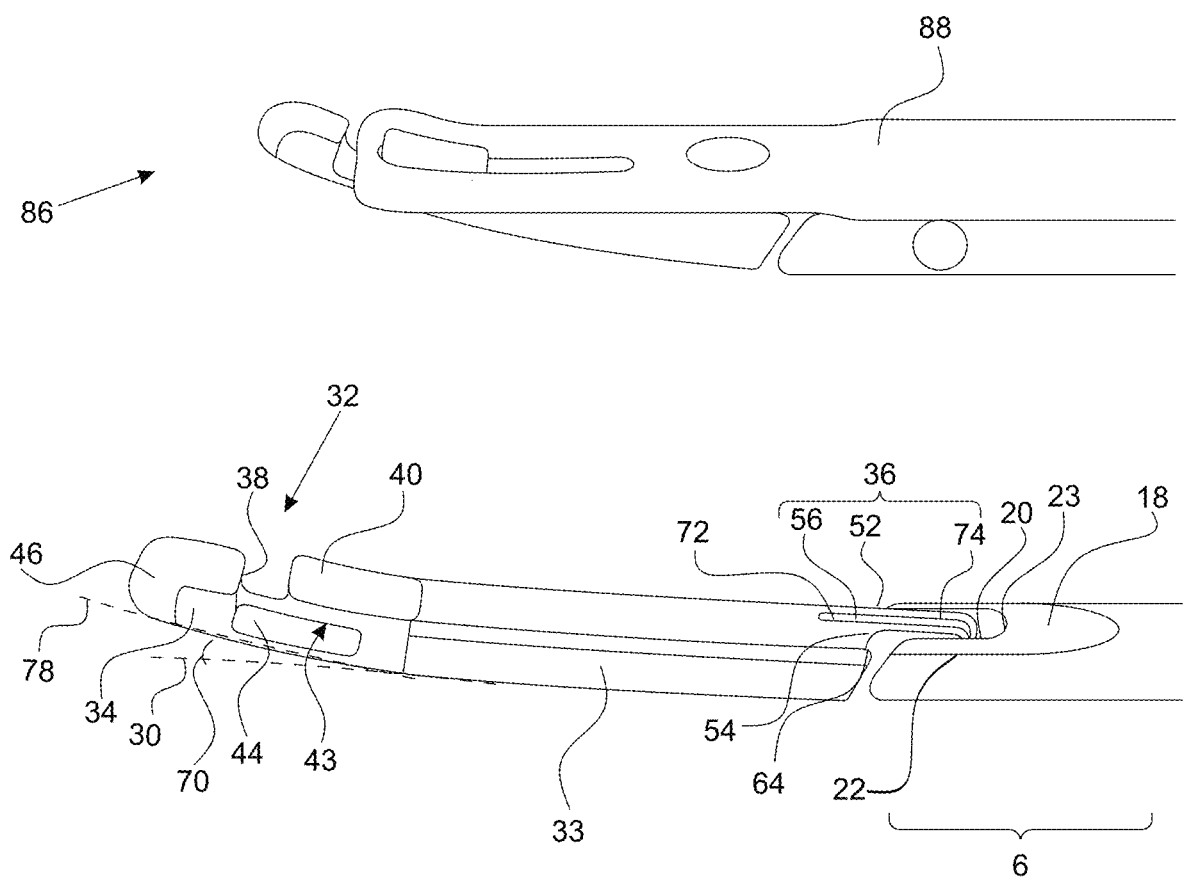
FIG. 18 depicts a close up of a tip manipulation member of a clamp installation tool with a clamp and without a clamp, wherein the clamp installation tool is in a coaxial configuration.

With reference to FIGS. 4, 5, 6, 16, and 24, in various instances, the retention hook 32 also includes a finger aspect placement boss 42. The finger aspect 40 may be spaced apart from the angled tip 34 of the tip manipulation member 10 so as to provide a boundary of the clamp channel 43 opposite the angled tip 34. To effectuate this spacing, there may be a local thickening of the tip manipulation member main body 33 connecting the finger aspect 40 to the tip manipulation member main body 33 and spacing the finger aspect 40 apart from the angled tip 34. This local thickening may be the finger aspect placement boss 42. In various embodiments, the finger aspect placement boss 42 comprises a ramp angled parallel to an aspect of the angled tip 34, such as being parallel to the angled tip minor longitudinal axis 48 (FIGS. 5, 18). The ramp may have an at least partially cylindrical profile, for instance, having a partially hemispheric cross-section of increasing radius at points approaching the finger aspect along the angled tip minor longitudinal axis, or having a constant radius but rising further from the tip manipulation member main body 33 such that the cross-sectional profile of the finger aspect placement boss 42 has an increasing arc length.

Figure 6:
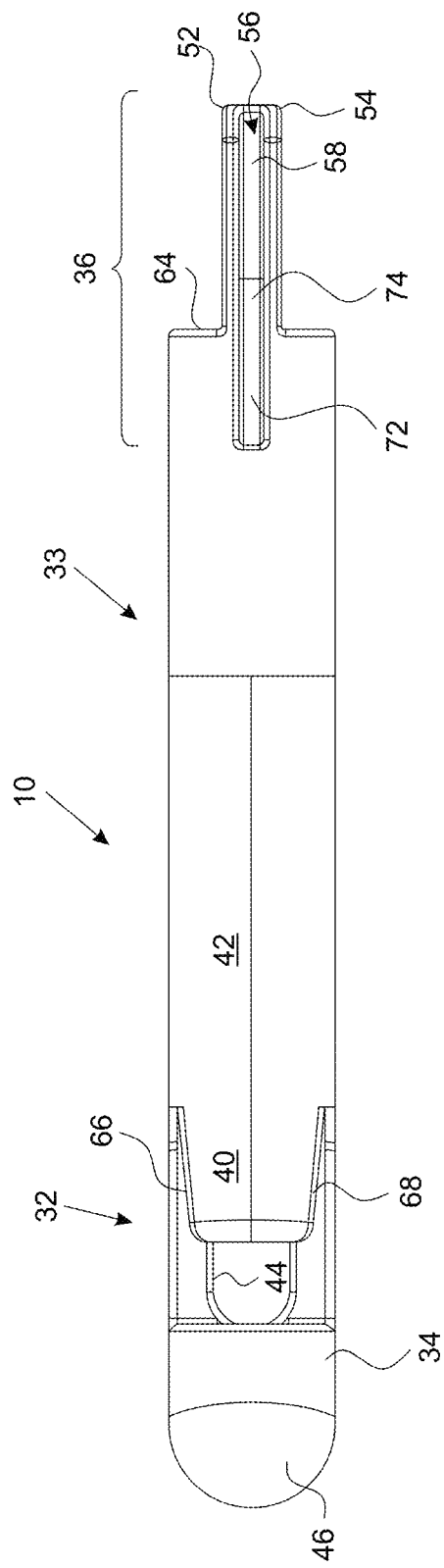
FIG. 6 is a top view of a tip manipulation member of a clamp installation tool.
Figure 7:
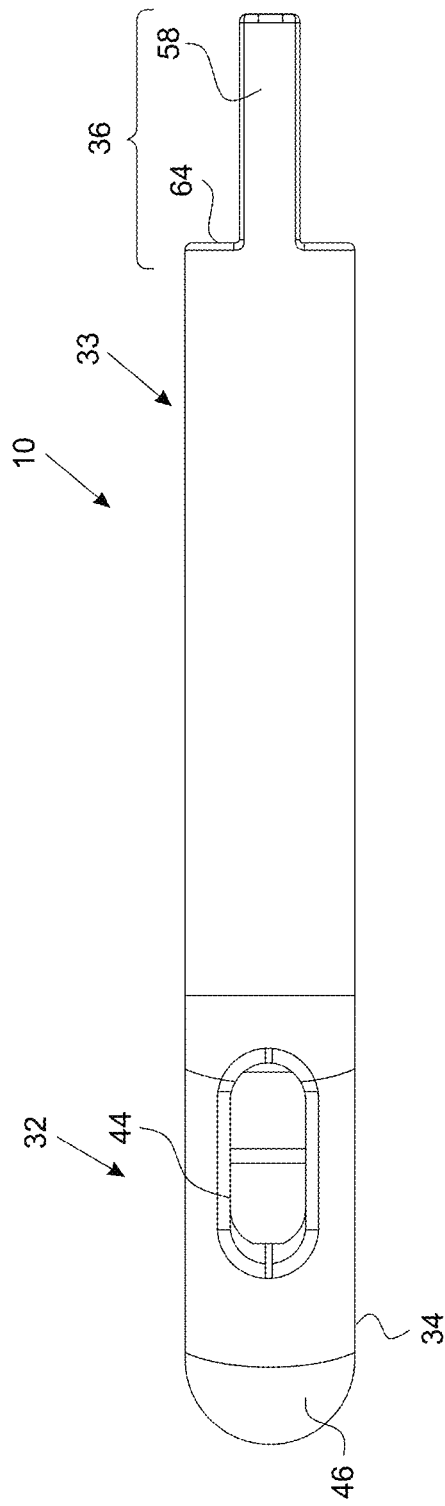
FIG. 7 is a bottom view of a tip manipulation member of a clamp installation tool.

With particular focus now on FIGS. 6 and 7, in various instances the finger aspect 40 comprises a first finger aspect convergent side 66 and a second finger aspect convergent side 68. Each of the first finger aspect convergent side 66 and the second finger aspect convergent side 68 comprise opposite edges of the finger aspect 40 extending along the longer edges of the finger aspect 40 (e.g., the lateral sides relative to the longitudinal direction). In various instances, the first finger aspect convergent side 66 and the second finger aspect convergent side 68 angle toward one another along the length of the finger aspect 40, narrowing toward the distal cantilevered tip of the finger aspect 40. In this manner, the finger aspect 40 tapers, facilitating insertion of the clamp 88 (FIGS. 9-15, 17-20, 22-23, 36-37) into the clamp channel 43 of the retention hook 32.

In various embodiments, the retention hook 32 further comprises a clamp channel 43, as shown in FIGS. 5, 16, 18, and 24. The clamp channel 43 comprises an opening defined on one side by the guidance ramp 38, on another side by the finger aspect 40 and potentially on another side by the angled tip 34 and configured to receive an aspect of a clamp 88 (FIGS. 9-15, 17-20, 22-23, 36-37) such as a tip retention aperture 100 (FIGS. 9, 10, 19, 22, 23) in selectable mechanical communication as the clamp installation tool 2 actuates, such as between a coaxial configuration 80 (FIG. 14) and an actuated configuration 82 (FIG. 15, 29). The clamp channel 43 may have a clamp channel opening 47 comprising a passage whereby the clamp 88 may be selectably inserted between the finger aspect 40 and the angled tip 34, then slidably transitioned off-axis from the travel path that it followed while being inserted between the finger aspect 40 and the angled tip 34, slidably transitioning into a retention space 49. The retention space 49 may be disposed medially between the clamp channel opening 47 and the clamp channel floor 51, such that a tension induced by stretching of the clamp 88 causes the clamp 88 to be biased toward the clamp channel floor 51, thereby being selectably retained within the clamp channel 43.

Finally, and with reference to FIGS. 4, 6, 7, 16, 18, and 24, the retention hook 32 may comprise a clamp release aperture 44. A clamp release aperture 44 may comprise an aperture extending through the angled tip 34 and into the clamp channel 43. The clamp release aperture 44 facilitates the selectable release of the clamp 88 from within the clamp channel 43 such as by setting an amount of static friction between the clamp 88 and the clamp channel 43 in response to the clamp release aperture 44 sizing and/or such as by facilitating the insertion of a tool to urge the clamp 88 out of the clamp channel 43.

Returning attention to FIGS. 4-7, 9, 16, and 18, the angled tip 34 is now discussed in greater detail, and reference is made to the safety dome 46. The angled tip 34 may comprise a safety dome 46 at the outermost distal end of the angled tip 34. The safety dome 46 may comprise a half-sphere structure disposed at the distal end of the tip manipulation member 10 opposite the tip manipulation member attachment mechanism 36. The safety dome 46 may, in further embodiments, comprise a chamfer, a rounding, an oval, a spheroid, or any shape as desired to soften a force concentration associated with the distal end of the tip manipulation member 10. For instance, as the clamp installation tool 2 is inserted into a body cavity, the safety dome 46 softens a force concentration associated with contact of the distal end of the tip manipulation member 10 to a body organ, diminishing the likelihood of catching against or scraping an organ, or penetrating a membrane.

Focusing on FIGS. 5 and 18, the angled tip 34 may have an angled tip minor longitudinal axis 48. An angled tip minor longitudinal axis 48 may comprise an axis extending through the angled tip 34 (FIGS. 4-9, 9, 16, 18) of the tip manipulation member 10 coincident with its center at all points along the axis.

Figure 9:
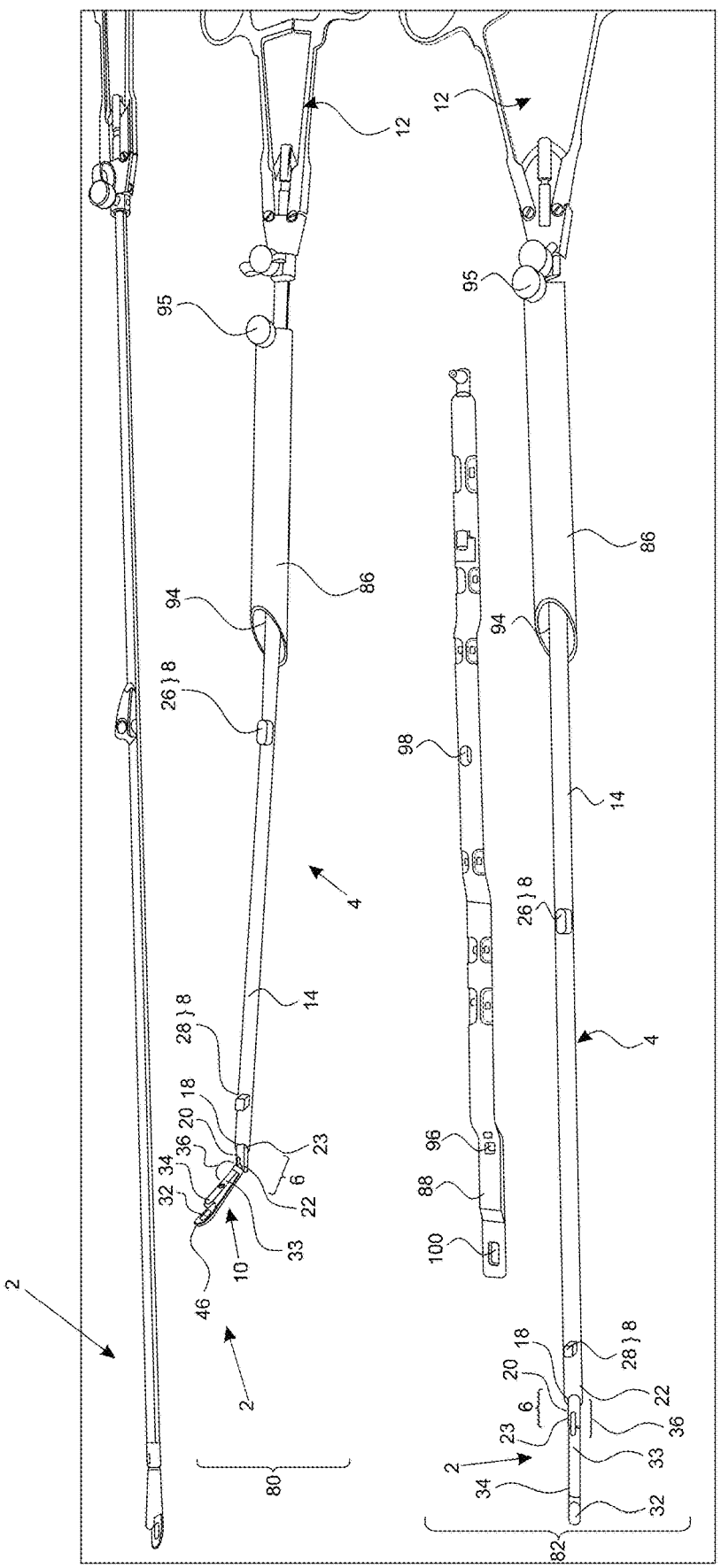
FIG. 9 depicts various example clamp installation tools and a clamp separate from a clamp installation tool.
Figure 10:
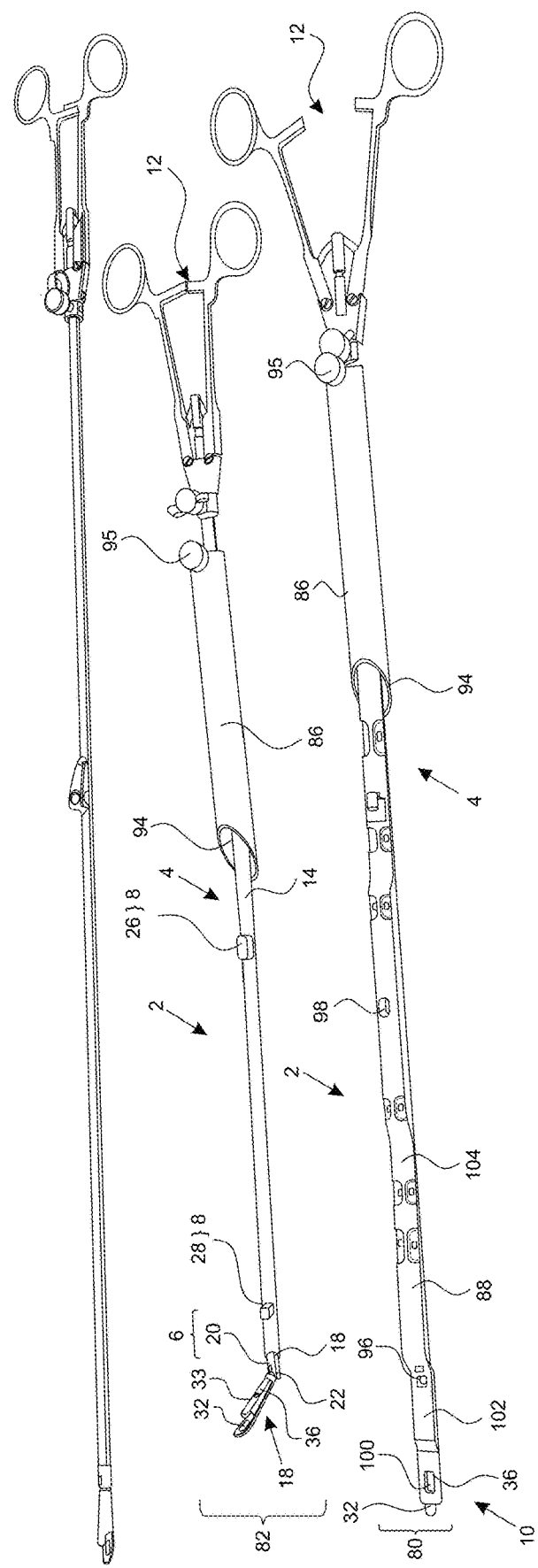
FIG. 10 depicts various example clamp installation tools and a clamp emplaced on a clamp installation tool.
Figure 11:
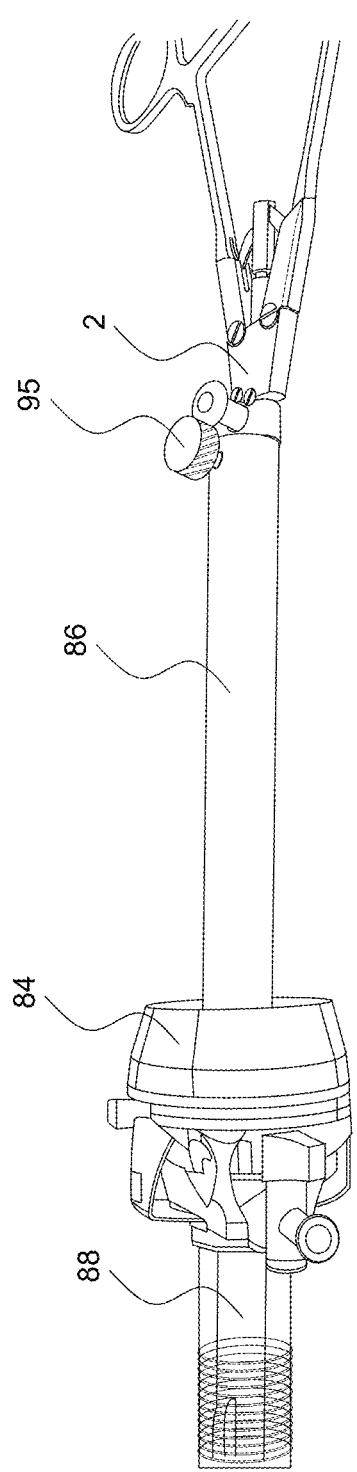
FIG. 11 depicts a clamp installation tool in simulated use with a trocar and inserted into the trocar.
Figure 12:
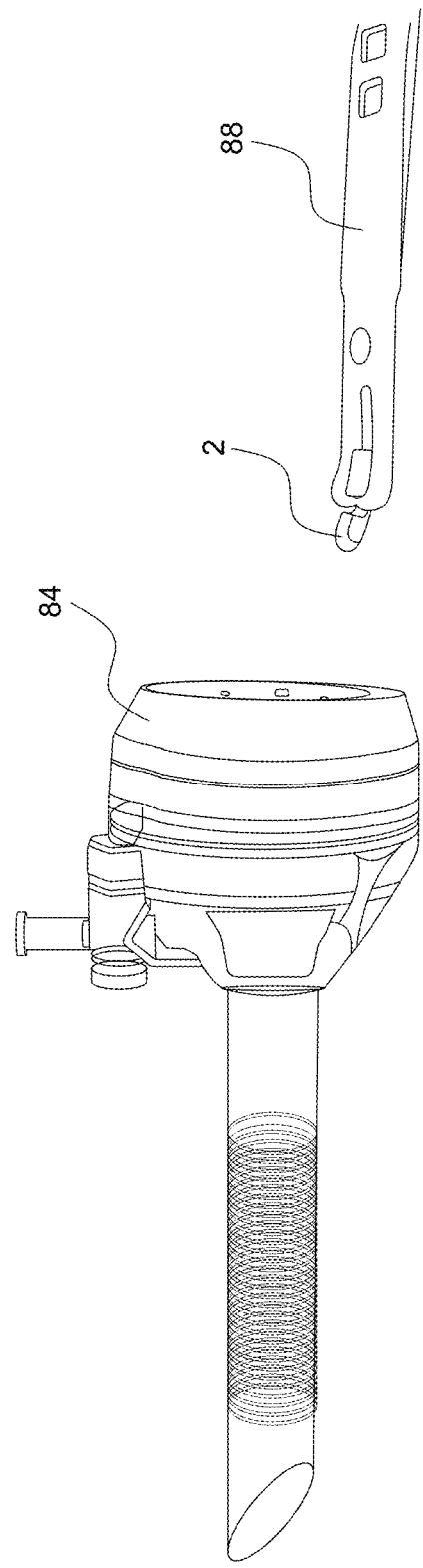
FIG. 12 depicts a clamp installation tool in simulated use with a trocar prior to insertion into the trocar.
Figure 13:
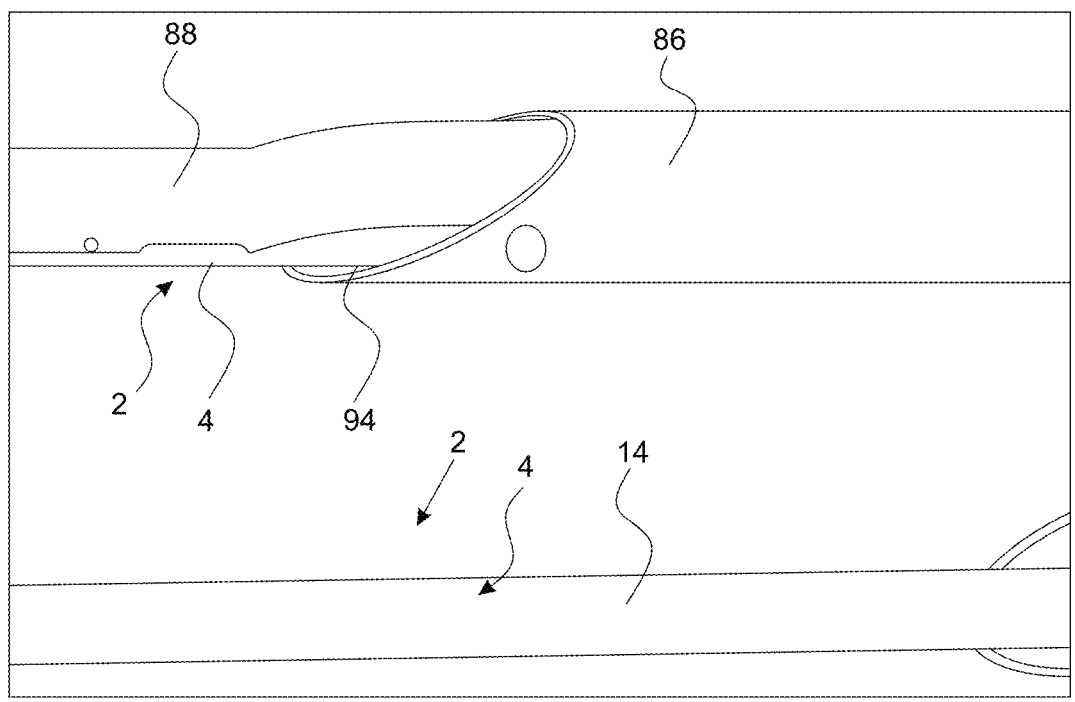
FIG. 13 depicts a close up view of a clamp installation tool with a sealing channel and a clamp.
Figure 19:
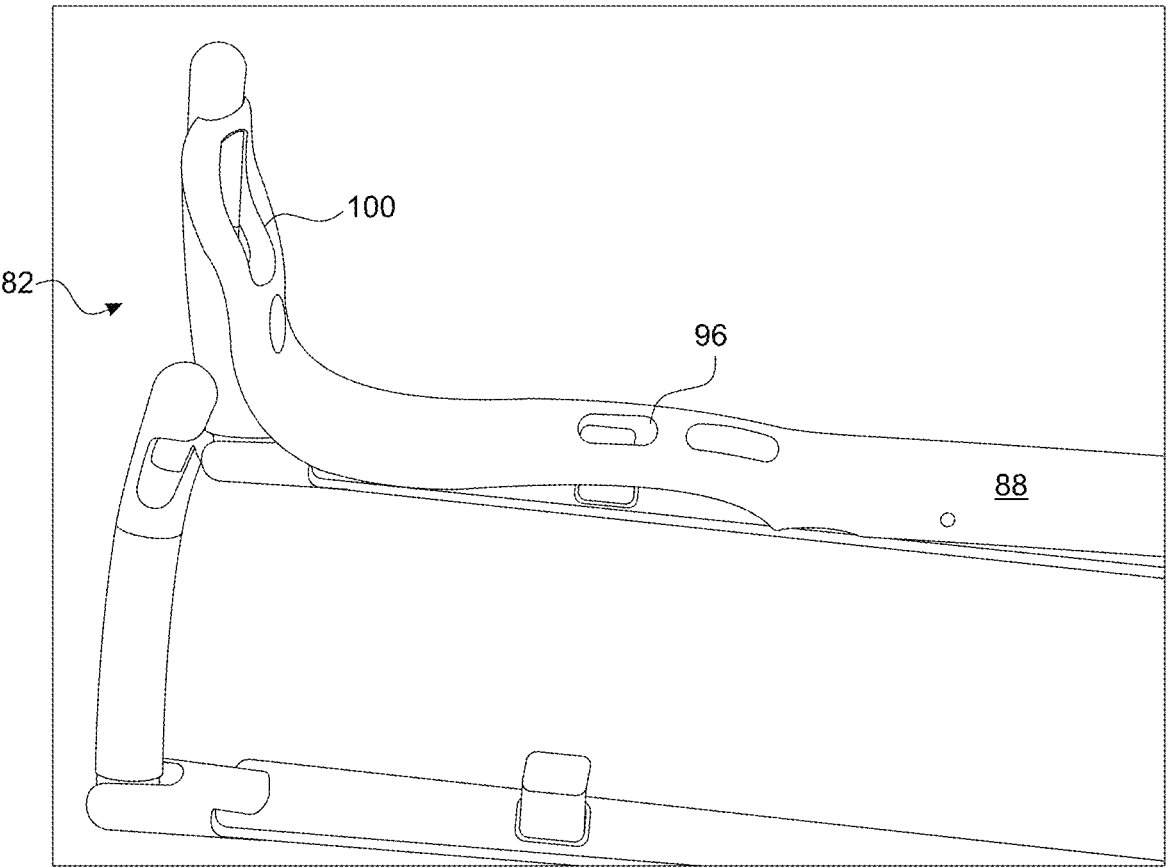
FIG. 19 depicts a close up of a tip manipulation member of a clamp installation tool with a clamp and without a clamp, wherein the clamp installation tool is in an actuated configuration.
Figure 20:
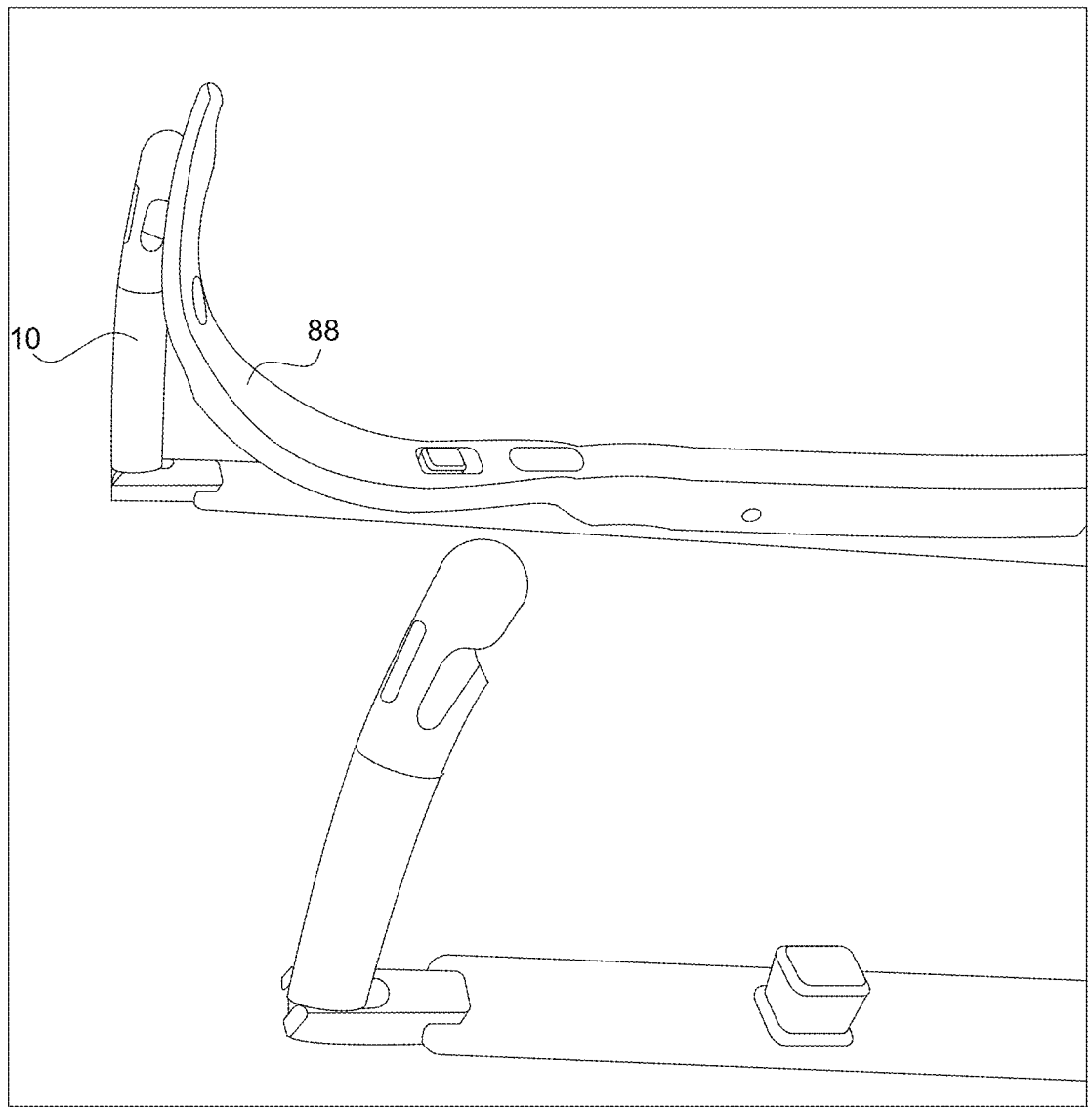
FIG. 20 depicts a close up of a tip manipulation member of a clamp installation tool with a clamp and without a clamp, wherein the clamp installation tool is in an actuated configuration and wherein the clamp is partially disconnected from the clamp installation tool.
Figure 21:
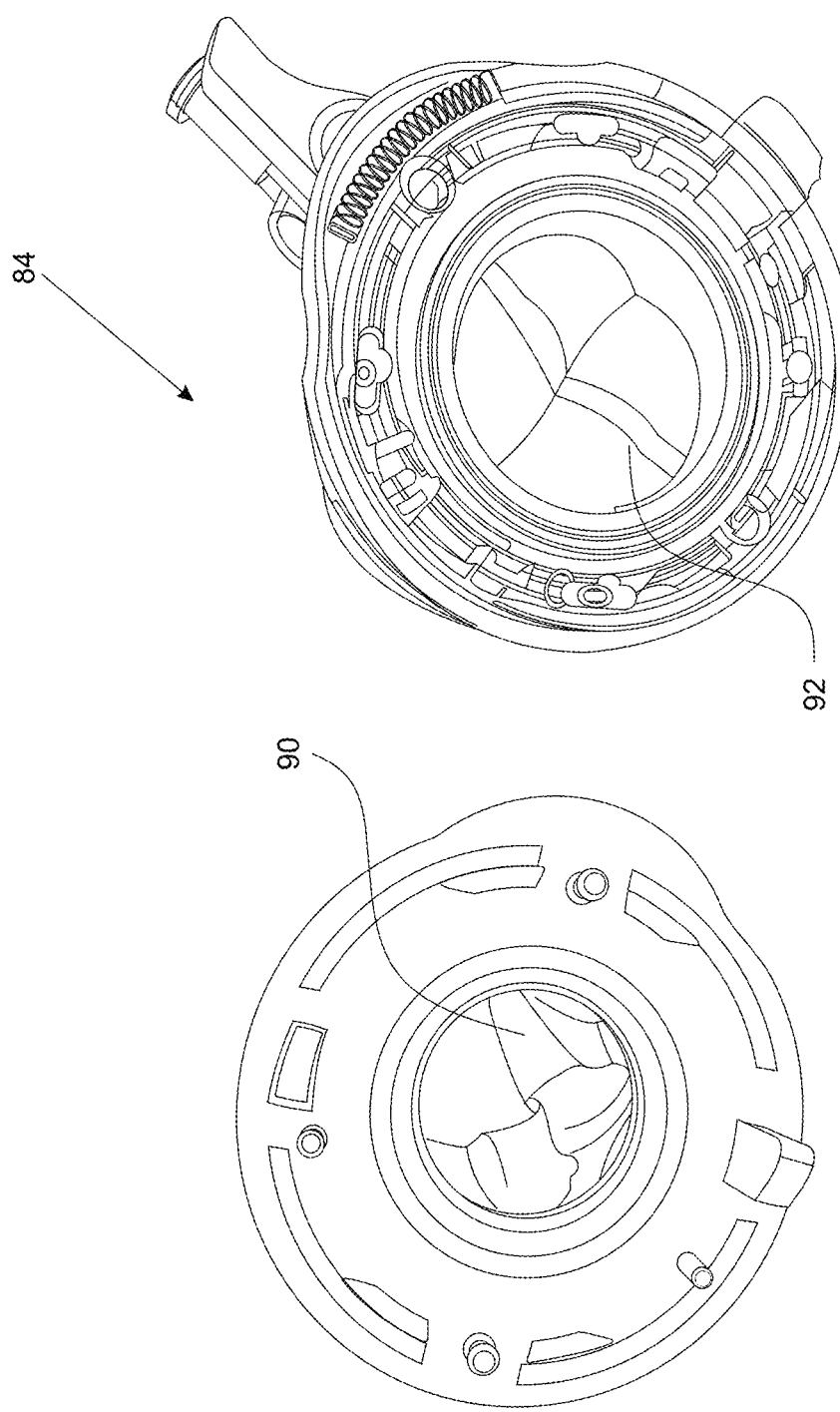
FIG. 21 depicts aspects of a partially disassembled trocar.
Figure 22:
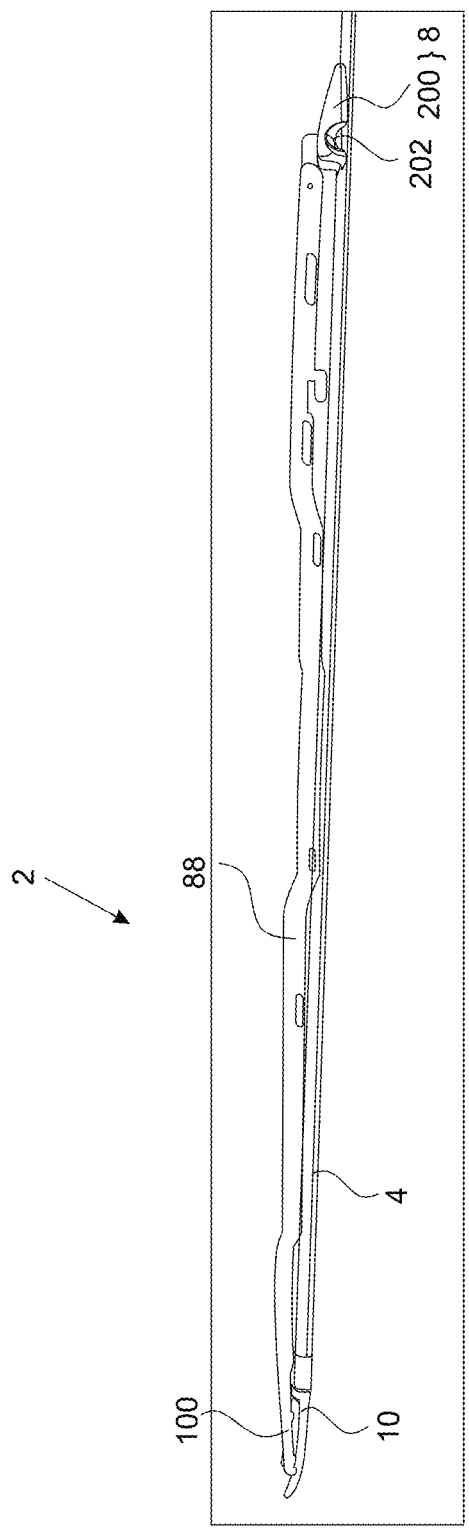
FIG. 22 depicts a view of an example embodiment of aspects of a clamp installation tool having a selectable retention mechanism with an end point ramp.
Figure 23:
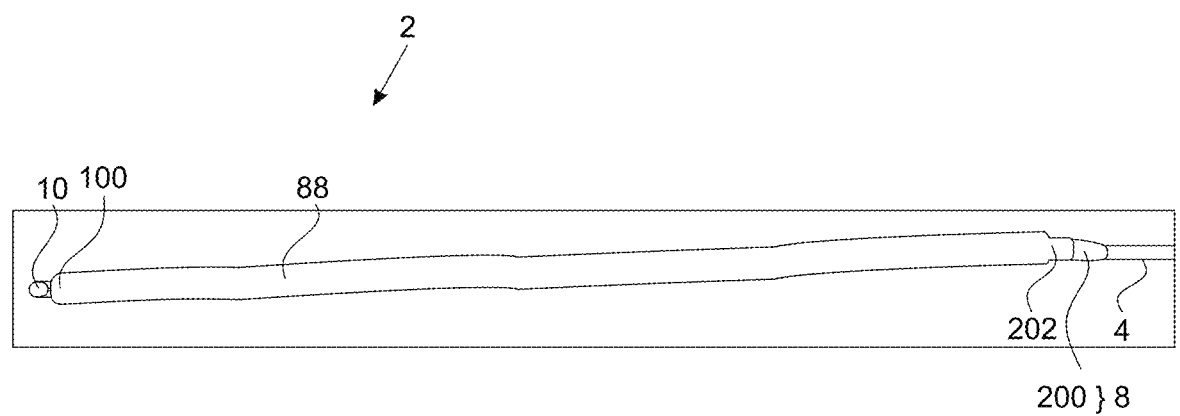
FIG. 23 depicts another view of an example embodiment of aspects of a clamp installation tool having a selectable retention mechanism with an end point ramp.
Figure 24:
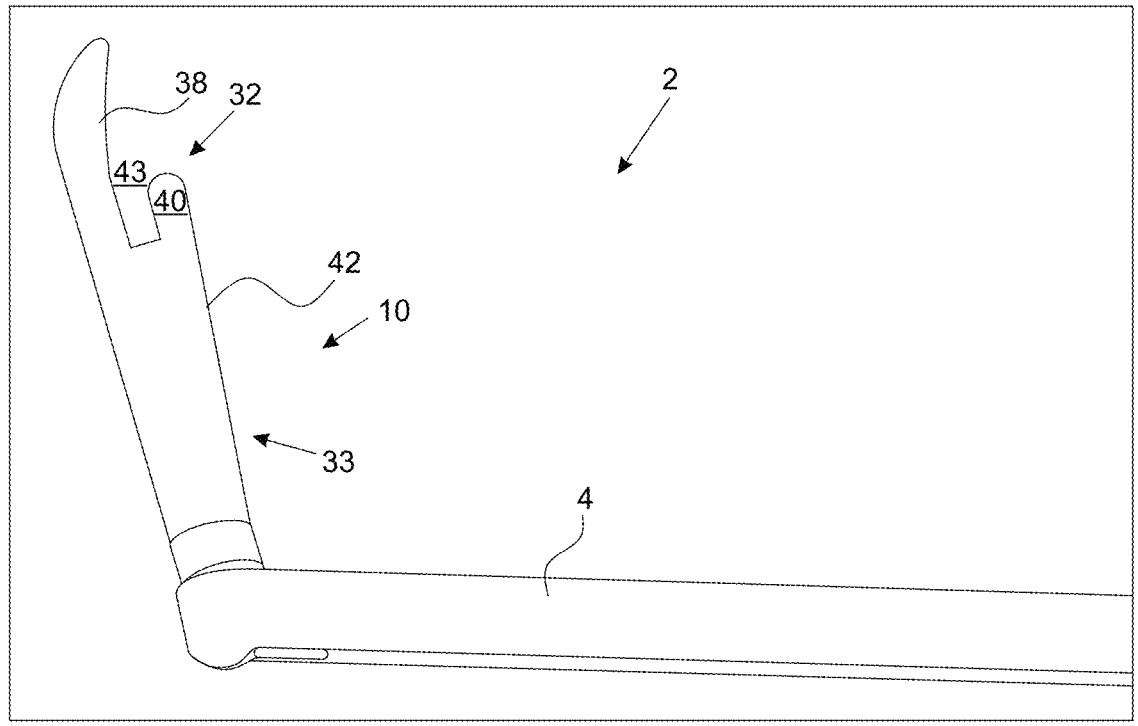
FIG. 24 depicts a view of an example embodiment of aspects of a tip articulation member of a clamp installation tool.
Figure 25:
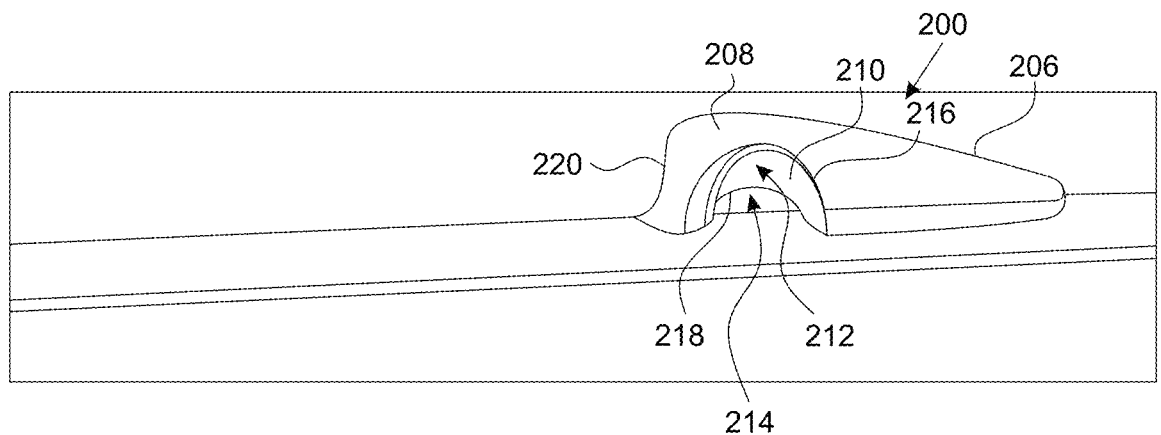
FIG. 25 depicts a side view of an example end point ramp of a selectable retention mechanism of a clamp installation tool.
Figure 26:
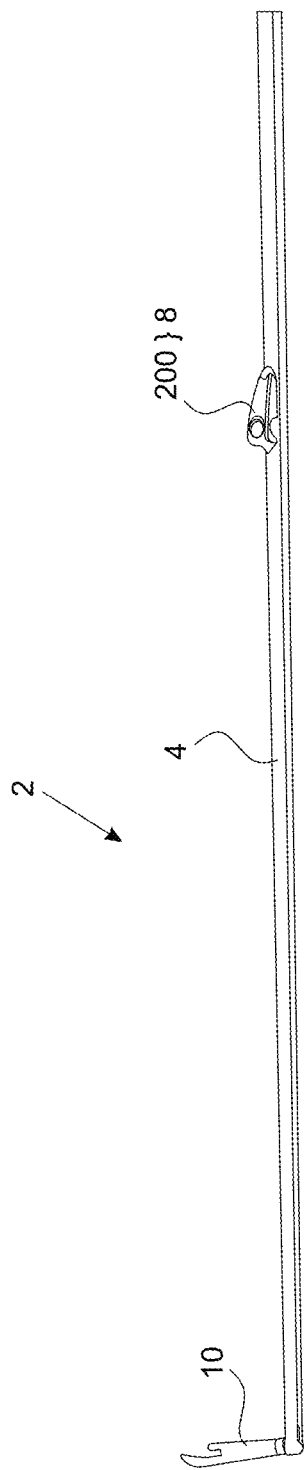
FIG. 26 depicts another view of an example embodiment of aspects of a clamp installation tool having a selectable retention mechanism with an end point ramp and a tip articulation member wherein the clamp installation tool is in an actuated position.
Figure 27:
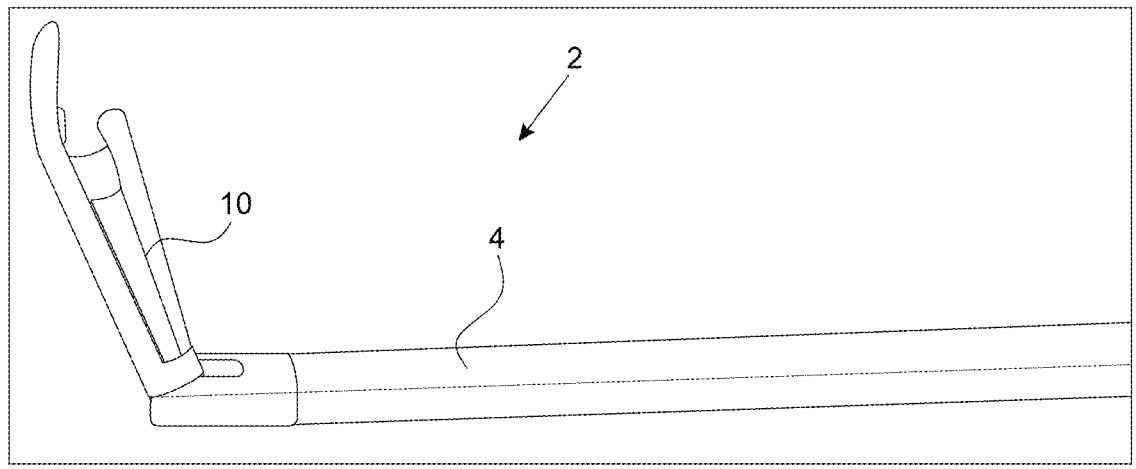
FIG. 27 depicts yet another view of an example embodiment of aspects of a clamp installation tool having a selectable retention mechanism with an end point ramp and a tip articulation member wherein the clamp installation tool is in an actuated position.
Figure 28:
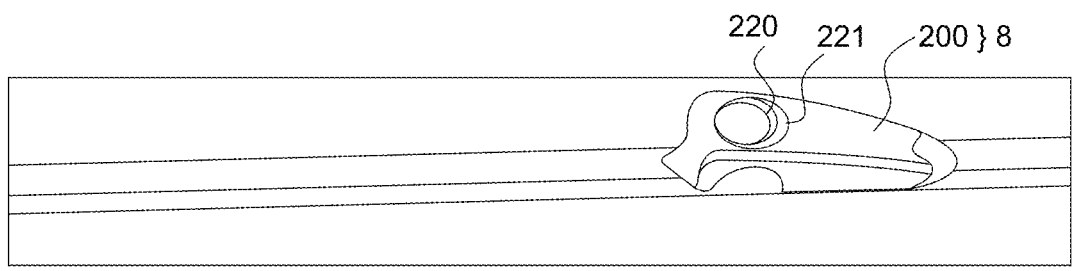
FIG. 28 depicts a top view of an example end point ramp of a selectable retention mechanism of a clamp installation tool.

A tip angle 70 may be defined between the angled tip minor longitudinal axis 48 and the tip manipulation member major longitudinal axis 30. In various embodiments, the tip angle 70 comprises an acute angle. In further instances, the tip angle 70 comprises a zero degree angle, such that the angled tip minor longitudinal axis 48 and the tip manipulation member major longitudinal axis 30 are coincident. In further instances, the tip angle 70 comprises a zero degree angle, such that the angled tip minor longitudinal axis 48 and the tip manipulation member major longitudinal axis 30 are parallel. In still further instances, the tip angle 70 comprises an obtuse angle, or a right angle, or any angle as desired. In various instances, the tip angle 70 is selected such that the clamp installation tool 2 is passable through a trocar 84 when in the coaxial configuration 80 (FIG. 14), and yet, such that the clamp 88 is not distorted by contact at the tip retention aperture 100 (FIGS. 9, 10, 19) of the clamp 88 with the clamp installation tool 2, but extends linearly from the tip retention aperture 100 (FIGS. 9, 10, 19). In further embodiments, the tip angle 70 is selected so that the clamp installation tool 2 is passable through a trocar 84 when in the coaxial configuration 80 (FIG. 14), and yet, such that the clamp 88 is spaced away from the clamp installation tool 2 at least along a portion of the length of the clamp 88.

In various embodiments, the angled tip 34 may comprise a relief inset 50. For instance, with reference to FIG. 5, a relief inset 50 comprises a chamfer, cutaway, or other localized thinning of the angled tip 34. In various instances, the relief inset 50 is oriented opposite the clamp channel 43. In further instances, the relief inset 50 is oriented opposite the clamp channel 43 and the clamp release aperture 44 extends from the relief inset 50 into the clamp release aperture 44.

Turning now to FIGS. 4, 5, 6, and 18, the tip manipulation member attachment mechanism 36 may comprise various aspects which will be detailed. For example, the tip manipulation member attachment mechanism 36 may comprise a first side flange 52 and a second side flange 54. Each of the first side flange 52 and second side flange 54 comprises a plate extending longitudinally outward from a distal end of the tip manipulation member main body 33. Each of the first side flange 52 and second side flange 54 extend parallel to the tip manipulation member major longitudinal axis 30 (FIG. 5). In various instances, a single first side flange 52 extends centered on the tip manipulation member major longitudinal axis 30, whereas in further instances, a first side flange 52 and second side flange 54 are spaced apart on opposite sides of the center of the tip manipulation member main body 33. The first side flange 52 and second side flange 54 extend from the end of the tip manipulation member 10 and are configured to be received within an aspect of the longitudinal main body 4 (FIGS. 1-3, 8-10, 13, 22, 24, 26, 29-37) such as the main body attachment mechanism 6 (FIGS. 1, 8-10, 18).

Referencing FIGS. 4, 6, and 18, the tip manipulation member attachment mechanism 36 includes a flange channel 56. A flange channel 56 comprises a space defined between the first side flange 52 and the second side flange 54 and further extending inwardly into the tip manipulation member main body 33 of the tip manipulation member 10 forming a cavity defined into the tip manipulation member main body 33. In various instances, the flange channel 56 has two portions, an offset channel section 74 comprising the portion of the flange channel 56 defined between the first side flange 52 and the second side flange 54, and an inset channel section 72 comprising the portion of the flange channel 56 defined inwardly into the tip manipulation member main body 33 of the tip manipulation member 10.

Referencing FIGS. 4, 5, 6, and 7, the tip manipulation member attachment mechanism 36 further includes an attachment mechanism flange web 58. The attachment mechanism flange web 58 comprises a web extending from the first side flange 52 to the second side flange 54. The attachment mechanism flange web 58 may have a longer side extending in a direction generally parallel to the longitudinal direction of the tip manipulation member 10, such as parallel the tip manipulation member major longitudinal axis 30. The attachment mechanism flange web 58 thus joins the first side flange 52 and the second side flange 54 to form a side of the flange channel 56. The attachment mechanism flange web 58 may comprise any shape configured to strengthen the first side flange 52 and the second side flange 54. In various instances, the attachment mechanism flange web 58 is omitted (see FIG. 18), such as depending on the material used to fabricate the tip manipulation member attachment mechanism 36.

With reference to FIGS. 4-5, the tip manipulation member attachment mechanism 36 may include a retention aperture 60. A retention aperture 60 may extend laterally (e.g., perpendicular to the tip manipulation member major longitudinal axis 30) through the first side flange 52 and the second side flange 54. The retention aperture 60 is configured to receive the retention pin 24 (FIG. 8) of the main body attachment mechanism 6 (FIG. 8) of the longitudinal main body 4 (FIG. 8). The retention aperture 60 may comprise an axis about which the tip manipulation member 10 may actuate relative to the longitudinal main body 4 (FIG. 8).

Figure 2:
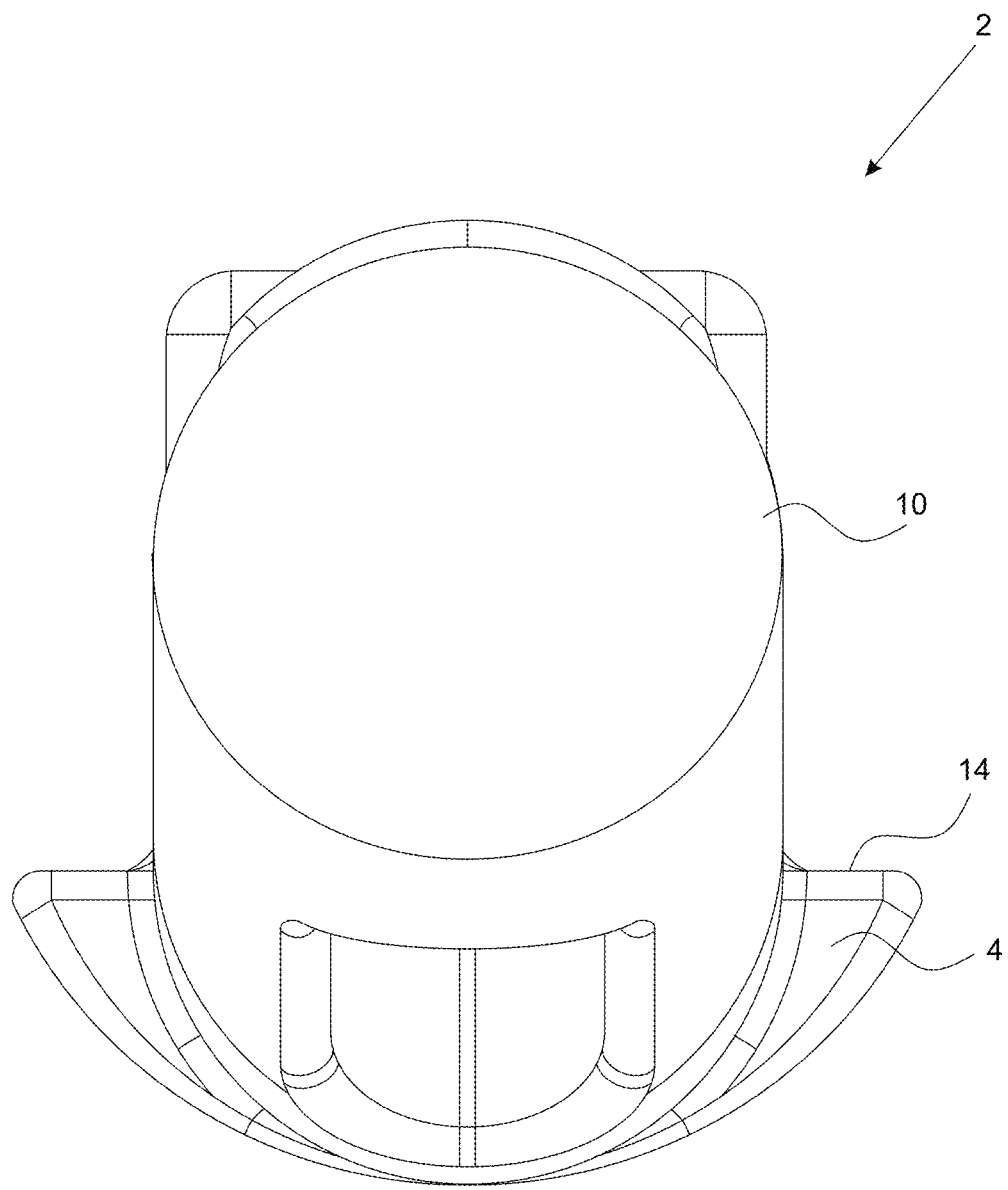
FIG. 2 is a first end view of an example embodiment of aspects of a clamp installation tool.

The tip manipulation member attachment mechanism 36 may also include an offset articulation aperture 62. The offset articulation aperture 62 may extend laterally (e.g., perpendicular to the tip manipulation member major longitudinal axis 30) through one or both of the first side flange 52 and the second side flange 54. The offset articulation aperture 62 is configured to receive a portion of a control aspect 12 (FIGS. 1, 9, 10) such as a control rod, control cable and/or the like that runs through the control rod channel 16 (FIGS. 2, 8) of the longitudinal main body 4 (FIGS. 2, 8). The offset articulation aperture 62 may be configured to receive a force, such as along a direction tangential to an arc centered on the retention aperture 60. As such, the pushing and/or pulling of the control aspect 12 (FIGS. 1, 9, 10) on the offset articulation aperture 62 may induce the tip manipulation member 10 to rotate about an axis provided by the retention aperture 60, actuating between a coaxial configuration 80 (FIG. 14) and an actuated configuration 82 (FIG. 15). The offset articulation aperture 62 may be spaced an articulation offset radius 78 from the retention aperture 60, the articulation offset radius 78 comprising a distance configured to provide a torque arm (e.g., a lever) whereby the linear travel of the control rod or cable is translated in to an arcuate motion of the offset articulation aperture 62 orbitally about the retention aperture 60 along an articulation path 76 comprising an arc.

Finally, with reference to FIGS. 4, 5, 6, 7, and 18, in various instances, an attachment butt plate 64 of the tip manipulation member attachment mechanism 36 comprises a face of the tip manipulation member main body 33 from which the first side flange 52 and/or second side flange 54 extends outward. In various embodiments, the attachment butt plate 64 comprises a contacting surface configured to contact against the longitudinal main body 4 and configured to limit the travel of the tip manipulation member 10 and thus the offset articulation aperture 62 along the articulation path 76, so that the orientation of the actuated configuration 82 (FIG. 15, 29) and/or coaxial configuration 80 (FIG. 14) is established.

With specific reference to FIGS. 9-11, and 13, a sealing channel 86 is provided. A sealing channel 86 comprises a hollow structure through which the clamp installation tool 2 may be inserted. For instance, in various embodiments, a clamp installation tool 2 with and/or without a clamp 88 attached thereto, may be desired to be inserted through a trocar 84. However, the shape of the clamp installation tool 2 and/or clamp 88 may cause unwanted fluid leakage (for instance, pressurized gas) through the trocar 84 alongside the clamp installation tool 2 and/or clamp 88. A sealing channel 86 may provide a shape configured to diminish this unwanted fluid leakage. For example, a sealing channel 86 may comprise a cylindrical tube. The sealing channel 86 may be slidably disposed over the clamp installation tool 2 while a clamp 88 is attached thereto, leaving only a small sealing channel gap 94 between the clamp 88 and/or clamp installation tool 2 and the sealing channel 86 so that only a minimal amount of fluid may escape. The combination of sealing channel 86, clamp installation tool 2, and clamp 88, may be slidably insertable into a trocar 84, for instance, with reference to FIGS. 11, 12, 14, 15, and 21, a trocar 84 having a first seal 90 and a second seal 92. In this manner, leakage of fluid through the trocar 84 is ameliorated.

The sealing channel 86 may comprise a sealing channel fastener 95. A sealing channel fastener 95 may comprise a mechanism whereby the sealing channel 86 is selectably engagable to the clamp installation tool 2. For example, the sealing channel 86 may be frictionally engagable to the clamp installation tool 2. In various embodiments, the sealing channel fastener 95 comprises a finger-tightenable bolt extending inwardly through the sealing channel 86 into the internal area of the sealing channel 86 and capable of pressing against the clamp installation tool 2.

Finally, and with reference to FIGS. 9-15, and 17-20, a clamp 88 is provided. The clamp 88 may be insertable into a body by the clamp installation tool 2 and installed on an organ. The clamp 88 may have aspects configured to interface with aspects of the clamp installation tool 2, such as to selectably retain the clamp 88 in mechanical communication with the clamp installation tool 2 during emplacement, then to selectably release the clamp 88 from mechanical communication with the clamp installation tool 2 once emplaced.

As mentioned, the clamp 88 may have a distal retention aperture 96, an intermediate retention aperture 98, and a tip retention aperture 100. The clamp 88 may be installed onto the clamp installation tool 2, with the distal retention aperture 96 attached to the distal boss 28 of the selectable retention mechanism 8 of the clamp installation tool 2, with the intermediate retention aperture 98 attached to the intermediate boss 26 of the selectable retention mechanism 8 of the clamp installation tool 2, and with the tip retention aperture 100 attached to the retention hook 32 of the tip manipulation member 10 of the clamp installation tool 2. The clamp installation tool 2 may be configured in the coaxial configuration 80 (FIG. 14). As such, a tension may be exerted on the clamp 88. A first tensioned clamp section 102 of the clamp 88 extends between the tip retention aperture 100 and the distal retention aperture 96. A second tensioned clamp section 104 of the clamp 88 extends between the distal retention aperture 96 and the intermediate retention aperture 98. The tension within each of the first tensioned clamp section 102 and the second tensioned clamp section 104 may be the same and/or may be different. The clamp installation tool 2 may be inserted through a trocar 84 into a body cavity and proximate to an organ desired to be clamped. The clamp installation tool 2 may be actuated by a control aspect 12 so that the clamp installation tool 2 changes from a coaxial configuration 80 to an actuated configuration 82. In the actuated configuration 82, the tension in the first tensioned clamp section 102 extending between the tip retention aperture 100 may unload, so that the tip retention aperture 100 is more loosely connected to the retention hook 32. However, the tension in the second tensioned clamp section 104 extending between the intermediate retention aperture 98 and the distal retention aperture 96 may increase, securely retaining the clamp 88 in position relative to the clamp installation tool 2 while the loosened tip retention aperture 100 is manipulated. In various embodiments, a separate tool may be used to grasp the clamp 88 proximate to the tip retention aperture 100 and selectably disconnect the tip retention aperture 100 from the clamp installation tool 2. The separate tool may be used to further position the clamp 88 relative to the organ. The clamp 88 may be emplaced and subsequently disconnected from the clamp installation tool 2. The clamp installation tool 2 is thereafter actuated to the coaxial configuration 80 and retracted from the body cavity through the trocar 84, leaving the clamp 88 emplaced within the body cavity.

In further instances, the clamp 88 may have an aft end retention nub 202 comprising an extension projecting normal to a surface of the clamp 88 at an end of the clamp 88. The aft end retention nub 202 may be receivable by an aspect of the selectable retention mechanism 8, such as an end point ramp 200 (FIG. 25, 26, 29) while the tip retention aperture 100 (FIG. 9, 10, 19, 22, 23) is attachable to the tip manipulation member 10 so that the intervening bosses of the selectable retention mechanism 8 may be omitted. As the clamp installation tool 2 articulates between coaxial configuration and actuated configuration, tension may be released along the entire length of the clamp 88.

In still further instances, the clamp 88 may be retained proximate to the clamp installation tool 2 by one or more clip 244 (FIG. 36-37). In various embodiments, clip 244 (FIG. 36-37) is a metal clip. Clip 244 (FIG. 36-37) may be a metal clip. Clip 244 (FIG. 36-37) may be C-shaped.

A number of additional and alternative embodiments of the surgical clamps, installation tools and methods for installing can have characteristics that are different from those described above. For example, it is envisioned that a surgical clamp 88 not intended for bariatric surgery might not have a passage forming section, and that such a clamp 88 might be smaller or larger, depending on the purpose of the clamp 88. For example, the clamp 88 can be one-tenth of an inch in length to partition a blood vessel, or twenty-two centimeters in length to partition a stomach. Moreover, the clamp 88 can be configured to partition any internal organ, and can vary in length accordingly between these two example lengths, or be longer or shorter as required. Moreover, it is envisioned that the clamp installation tool 2 can be integrated with an endoscope and/or surgical robot and that appropriate robotic elements can be included in place of or in addition to those described above. These and other features can be included in various combinations without departing from the scope of the invention as defined in the following aspects.

The invention claimed is:

1. A clamp installation tool comprising:
   a longitudinal main body comprising an elongate member having a longitudinal support platform configured to support a clamp;
   a selectable retention mechanism configured to connect to the clamp;
   a tip manipulation member coupled to a distal end of the longitudinal main body and arcuately articulable relative to the longitudinal main body; and
   a control aspect configured to articulate the tip manipulation member,
   wherein the control aspect comprises a single use grip comprising:
      an actuator configured to articulate the tip manipulation member; and
      a safety configured to inhibit operation of the actuator.

2. The clamp installation tool according to claim 1, wherein the longitudinal main body is made of plastic.

3. The clamp installation tool according to claim 1, wherein the longitudinal main body further comprises:
   a control rod channel configured to receive a control rod extending through the longitudinal main body and connecting the tip manipulation member to a control aspect;
   a main body attachment mechanism configured to attach to the tip manipulation member.

4. The clamp installation tool according to claim 1, further comprising a sealing channel comprising a cylindrical tube receivable over the clamp installation tool and insertable into a trocar.

5. A clamp installation tool comprising:
   a longitudinal main body comprising an elongate member having a longitudinal support platform configured to support a clamp;
   a selectable retention mechanism configured to connect to the clamp; and
   a tip manipulation member coupled to a distal end of the longitudinal main body and arcuately articulable relative to the longitudinal main body, wherein the selectable retention mechanism comprises an end point ramp configured to receive an aft end retention nub of the clamp.

6. The clamp installation tool according to claim 5, wherein the longitudinal main body is made of metal.

7. The clamp installation tool according to claim 5, wherein the tool is a single-use tool.

8. The clamp installation tool according to claim 5, wherein the tool is reusable.

9. A clamp installation tool comprising:
a longitudinal main body comprising an elongate member having a longitudinal support platform configured to support a clamp;
a selectable retention mechanism configured to connect to the clamp; and
a tip manipulation member coupled to a distal end of the longitudinal main body and arcuately articulable relative to the longitudinal main body,
wherein the selectable retention mechanism comprises an aft nub capture boss having a clamp receiving passage configured to receive an aft end retention nub of the clamp.

10. A clamp installation tool comprising:
a longitudinal main body comprising an elongate member having a longitudinal support platform configured to support a clamp;
a selectable retention mechanism configured to connect to the clamp; and
a tip manipulation member coupled to a distal end of the longitudinal main body and arcuately articulable relative to the longitudinal main body,
wherein the selectable retention mechanism comprises a lateral reaction plate comprising a reaction wall configured to press against an aft end retention nub of the clamp.

11. A clamp installation tool comprising:
a longitudinal main body comprising an elongate member having a longitudinal support platform configured to support a clamp;
a selectable retention mechanism configured to connect to the clamp; and
a tip manipulation member coupled to a distal end of the longitudinal main body and arcuately articulable relative to the longitudinal main body,
wherein the longitudinal main body further comprises:
a control rod channel configured to receive a control rod extending through the longitudinal main body and connecting the tip manipulation member to a control aspect;
a main body attachment mechanism configured to attach to the tip manipulation member, and
wherein the main body attachment mechanism comprises:
a cantilevered boss extending from the longitudinal main body;
a first main body side flange and a second main body side flange extending from the cantilevered boss and defining a main body flange channel disposed between the first main body side flange and the second main body side flange; and
a retention pin configured to retain the tip manipulation member in attachment to the main body attachment mechanism.

12. The clamp installation tool according to claim 11, wherein the tip manipulation member comprises:
a manipulation member main body extending outwardly from an attachment mechanism configured to connect to the main body attachment mechanism; and
a retention hook extending from the manipulation member main body and wherein the retention hook is configured to receive a tip retention aperture of the clamp.

13. A clamp installation tool comprising:
a longitudinal main body comprising an elongate member having a longitudinal support platform configured to support a clamp;
a selectable retention mechanism configured to connect to the clamp; and
a tip manipulation member coupled to a distal end of the longitudinal main body and arcuately articulable relative to the longitudinal main body,
wherein the longitudinal main body further comprises:
a control rod channel configured to receive a control rod extending through the longitudinal main body and connecting the tip manipulation member to a control aspect;
a main body attachment mechanism configured to attach to the tip manipulation member,
wherein the tip manipulation member comprises:
a manipulation member main body extending outwardly from an attachment mechanism configured to connect to the main body attachment mechanism; and
a retention hook extending from the manipulation member main body and wherein the retention hook is configured to receive a tip retention aperture of the clamp,
wherein the tip manipulation member comprises an attachment mechanism comprising:
a first side flange and a second side flange extending outwardly from the manipulation member main body and spaced apart to provide a flange channel;
an attachment mechanism flange web connecting the first side flange and the second side flange;
a retention aperture disposed through the first side flange and the second side flange and wherein the retention aperture is configured to receive the retention pin of the main body attachment mechanism to permit articulation of the tip manipulation member about an axis provided by the retention pin and along an articulation path; and
an offset articulation aperture spaced an articulation offset radius from the retention aperture and wherein the offset articulation aperture is configured to connect to the control rod.

14. The clamp installation tool according to claim 13, wherein the tip manipulation member comprises an angled tip comprising a safety dome at the outermost distal end of the tip manipulation member, the safety dome comprising a half-hemisphere.

15. A method of constructing a clamp installation tool comprising:
providing a longitudinal main body comprising an elongate member having a longitudinal support platform configured to support a clamp;
providing a selectable retention mechanism configured to connect to the clamp;
providing a tip manipulation member coupled to a distal end of the longitudinal main body and arcuately articulable relative to the longitudinal main body; and
providing a control aspect configured to articulate the tip manipulation member, wherein providing the control aspect comprises providing a single use grip comprising:

an actuator configured to articulate the tip manipulation member; and a safety configured to inhibit operation of the actuator.

16. A clamp installation tool comprising:

a longitudinal main body comprising an elongate member having a longitudinal support platform configured to support a clamp;

a selectable retention mechanism configured to connect to the clamp; and a tip manipulation member coupled to a distal end of the longitudinal main body and arcuately articulable relative to the longitudinal main body, wherein the longitudinal main body further comprises:

a control rod channel configured to receive a control rod extending through the longitudinal main body and connecting the tip manipulation member to a control aspect;

a main body attachment mechanism configured to attach to the tip manipulation member;

wherein the main body attachment mechanism comprises:

a cantilevered boss extending from the longitudinal main body;

a first main body side flange and a second main body side flange extending from the cantilevered boss and defining a main body flange channel disposed between the first main body side flange and the second main body side flange; and a retention pin configured to retain the tip manipulation member in attachment to the main body attachment mechanism;

wherein the tip manipulation member comprises:

a manipulation member main body extending outwardly from an attachment mechanism configured to connect to the main body attachment mechanism; and a retention hook extending from the manipulation member main body and wherein the retention hook is configured to receive a tip retention aperture of a clamp;

an angled tip comprising a safety dome at the outermost distal end of the tip manipulation member, the safety dome comprising a half-hemisphere;

wherein the attachment mechanism of the tip manipulation member comprises:

a first side flange and a second side flange extending outwardly from the manipulation member main body and spaced apart to provide a flange channel;

an attachment mechanism flange web connecting the first side flange and the second side flange;

a retention aperture disposed through the first side flange and the second side flange and wherein the retention aperture is configured to receive the retention pin of the main body attachment mechanism to permit articulation of the tip manipulation member about an axis provided by the retention pin and along an articulation path; and an offset articulation aperture spaced an articulation offset radius from the retention aperture and wherein the offset articulation aperture is configured to connect to the control rod.

\* \* \* \* \*

UNITED STATES PATENT AND TRADEMARK OFFICE
CERTIFICATE OF CORRECTION

PATENT NO. : 10,932,938 B2
APPLICATION NO. : 16/044382
DATED : March 2, 2021
INVENTOR(S) : French Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 235 days.

Signed and Sealed this
Thirty-first Day of January, 2023

*Katherine Kelly Vidal*

Katherine Kelly Vidal
*Director of the United States Patent and Trademark Office*